(12) United States Patent
Arrington et al.

(10) Patent No.: US 7,169,788 B2
(45) Date of Patent: Jan. 30, 2007

(54) TYROSINE KINASE INHIBITORS

(75) Inventors: Kenneth L. Arrington, Elkins Park, PA (US); Mark E. Fraley, North Wales, PA (US); George D. Hartman, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 372 days.

(21) Appl. No.: 10/489,647

(22) PCT Filed: Oct. 25, 2002

(86) PCT No.: PCT/US02/34379

§ 371 (c)(1),
(2), (4) Date: Mar. 15, 2004

(87) PCT Pub. No.: WO03/037252

PCT Pub. Date: May 8, 2003

(65) Prior Publication Data

US 2004/0220216 A1    Nov. 4, 2004

Related U.S. Application Data

(60) Provisional application No. 60/339,075, filed on Oct. 30, 2001.

(51) Int. Cl.
  *A61K 31/496* (2006.01)
  *A61K 31/4704* (2006.01)
  *C07D 401/04* (2006.01)
  *C07D 401/14* (2006.01)

(52) U.S. Cl. ............... 514/253.07; 514/312; 544/363; 546/157

(58) Field of Classification Search ............ 546/157; 544/363
See application file for complete search history.

(56) References Cited

U.S. PATENT DOCUMENTS

| 5,409,930 A | 4/1995 | Spada et al. |
| 6,306,874 B1 | 10/2001 | Fraley et al. |
| 2003/0028018 A1 | 2/2003 | Renhowe et al. |

FOREIGN PATENT DOCUMENTS

| WO | WO 92/20642 | 11/1992 |
| WO | WO 97/06144 | 2/1997 |
| WO | WO 97/19927 | 6/1997 |
| WO | WO 97/44037 | 11/1997 |
| WO | WO 98/23613 | 6/1998 |
| WO | WO 00/09495 | 2/2000 |

OTHER PUBLICATIONS

Emerging approaches to antiangiogenic therapies for treating cancer, posted Nov. 3, 2005 on http://www.nyas.org/ebriefreps/main.asp?intSubsectionID=3099 .*
Chinese Science Bulletin, vol. 36, No. 24, pp. 2056-2060 (1991), by J. Meng, et al.
Science in China, vol. 36, No. 5, pp. 540-549 (1993), by J. Meng, et al.
Oncogene, vol. 6, pp. 1677-1683 (1991), by B. Terman, et al.
J. Clin. Invest, vol. 104, No. 11, pp. 1613-1620 (1991), by N. van Bruggen, et al.
Drug News Perspect, vol. 11, No. 5, pp. 265-270 (1998), by D. Greenberg.
Nature, vol. 407, pp. 242-248 (2000), by G. Yancopoulos, et al.
Nature, vol. 407, pp. 249-257 (2000), by P. Carmeliet, et al.
J. Heterocyclic Chem., vol. 28, pp. 1481-1484 (1991), by R. Wang, et al.
Nature Biotech., vol. 17, pp. 963-968 (1999), by V. Brower.
Nature Medicine, vol. 5, No. 6, pp. 623-628 (1999), by H. Gerber, et al.
Molecular Cell, vol. 4, pp. 915-924 (1999), by B. Eliceiri, et al.
Stem Cells, vol. 12, pp. 1-6 (1994), by T. Burke, Jr.
Platelets, vol. 10, pp. 285-292 (1999), by A Amirkhosravi, et al.
FEBS Letters, vol. 473, pp. 161-164 (2000), by M. Nakagawa, et al.
Endocrinology, vol. 141, No. 5 pp. 1667-1674 (2000), by M. Deckers, et al.
Oncogene, vol. 5, pp. 519-524 (1990), by M. Shibuya, et al.
J. Med. Chem., vol. 37, pp. 2129-2137 (1994), by M. Maguire, et al.
J. Med. Chem., vol. 42, pp. 5369-5389, by L. Hennequin, et al.
Cancer Research 64, pp. 751-756, Jan. 15, 2004, by L. Sepp-Lorenzino, et al.
Bioorganic & Medicinal Chemistry Letters 14, (2004), pp. 351-355, by M. Fraley, et al.
Current Medicinal Chemistry 11, (2004), pp. 709-719, by M. Fraley, et al.

* cited by examiner

*Primary Examiner*—Emily Bernhardt
(74) *Attorney, Agent, or Firm*—Dianne Brown; Mark R. Daniel

(57) ABSTRACT

The present invention relates to compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

6 Claims, No Drawings

TYROSINE KINASE INHIBITORS

PRIORITY CLAIM

This application is a §371 application of PCT/US02/34379 that was filed on Oct. 25, 2002, which claims priority from the U.S. Provisional Application No. 60/339,075, that was filed on Oct. 30, 2001 and is now abandoned.

BACKGROUND OF THE INVENTION

The present invention relates to compounds which inhibit, regulate and/or modulate tyrosine kinase signal transduction, compositions which contain these compounds, and methods of using them to treat tyrosine kinase-dependent diseases and conditions, such as angiogenesis, cancer, tumor growth, atherosclerosis, age related macular degeneration, diabetic retinopathy, inflammatory diseases, and the like in mammals.

The following is provided as background information only and should not be taken as an admission that any subject matter discussed or that any reference mentioned is prior art to the instant invention Tyrosine kinases are a class of enzymes that catalyze the transfer of the terminal phosphate of adenosine triphosphate to tyrosine residues in protein substrates. Tyrosine kinases are believed, by way of substrate phosphorylation, to play critical roles in signal transduction for a number of cell functions. Though the exact mechanism of signal transduction is still unclear, tyrosine kinases have been shown to be important contributing factors in cell proliferation, carcinogenesis and cell differentiation.

Tyrosine kinases can be categorized as receptor type or non-receptor type. Receptor type tyrosine kinases have an extracellular, a transmembrane, and an intracellular portion, while non-receptor type tyrosine kinases are wholly intracellular.

The receptor-type tyrosine kinases are comprised of a large number of transmembrane receptors with diverse biological activity. In fact, about twenty different subfamilies of receptor-type tyrosine kinases have been identified. One tyrosine kinase subfamily, designated the HER subfamily, is comprised of EGFR, HER2, HER3, and HER4. Ligands of this subfamily of receptors include epithileal growth factor, TGF-α, amphiregulin, HB-EGF, betacellulin and heregulin. Another subfamily of these receptor-type tyrosine kinases is the insulin subfamily, which includes INS-R, IGF-IR, and IR-R The PDGF subfamily includes the PDGF-α and β receptors, CSFIR, c-kit and FLK-II. Then there is the FLK family which is comprised of the kinase insert domain receptor (KDR), fetal liver kinase-1 (FLK-1), fetal liver kinase-4 (FLK-4) and the fins-like tyrosine kinase-1 (flt-1). The PDGF and FLK families are usually considered together due to the similarities of the two groups. For a detailed discussion of the receptor-type tyrosine kinases, see Plowman et al., *DN&P* 7(6):334–339, 1994, which is hereby incorporated by reference.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen *Oncogene,* 8:2025–2031 (1993), which is hereby incorporated by reference.

Both receptor-type and non-receptor type tyrosine kinases are implicated in cellular signaling pathways leading to numerous pathogenic conditions, including cancer, psoriasis and hyperimmune responses.

Several receptor-type tyrosine kinases, and the growth factors that bind thereto, have been suggested to play a role in angiogenesis, although some may promote angiogenesis indirectly (Mustonen and Alitalo, *J. Cell Biol* 129:895–898, 1995). One such receptor-type tyrosine kinase is fetal liver kinase 1 or FLK-1. The human analog of FLK-1 is the kinase insert domain-containing receptor KDR, which is also known as vascular endothelial cell growth factor receptor 2 or VEGFR-2, since it binds VEGF with high affinity. Finally, the murine version of this receptor has also been called NYK (Oelrichs et al., *Oncogene* 8(1):11–15, 1993.) VEGF and KDR are a ligand-receptor pair that play an important role in the proliferation of vascular endothelial cells, and the formation and sprouting of blood vessels, termed vasculogenesis and angiogenesis, respectively.

Angiogenesis is characterized by excessive activity of vascular endothelial growth factor (VEGF). VEGF is actually comprised of a family of ligands (Klagsburn and D3 Amore, *Cytokine &Growth Factor Reviews* 7:259–270, 1996). VEGF binds the high affinity membrane-spanning tyrosine kinase receptor KDR and the related fms-like tyrosine kinase-1, also known as Flt-1 or vascular endothelial cell growth factor receptor 1 (VEGFR-1). Cell culture and gene knockout experiments indicate that each receptor contributes to different aspects of angiogenesis. KDR mediates the mitogenic function of VEGF whereas Flt-1 appears to modulate non-mitogenic functions such as those associated with, cellular adhesion. Inhibiting KDR thus modulates the level of mitogenic VEGF activity. In fact, tumor growth has been shown to be susceptible to the antiangiogenic effects of VEGF receptor antagonists. (Kim et al., Nature 362, pp. 841–844, 1993).

Solid tumors can therefore be treated by tyrosine kinase inhibitors since these tumors depend on angiogenesis for the formation of the blood vessels necessary to support their growth. These solid tumors include histiocytic lymphoma, cancers of the brain, genitourinary tract, lymphatic system, stomach, larynx and lung, including lung adenocarcinoma and small cell lung cancer. Additional examples include cancers in which overexpression-or activation of Raf-activating oncogenes (e.g., K-ras, erb-B) is observed. Such cancers include pancreatic and breast carcinoma. Accordingly, inhibitors of these tyrosine kinases are useful for the prevention and treatment of proliferative diseases dependent on these enzymes.

The angiogenic activity of VEGF is not limited to tumors. VEGF accounts for most of the angiogenic activity produced in or near the retina in diabetic retinopathy. This vascular growth in the retina leads to visual degeneration culminating in blindness. Ocular VEGF mRNA and protein are elevated by conditions such as retinal vein occlusion in primates and decreased $pO_2$ levels in mice that lead to neovascularization. Intraocular injections of anti-VEGF monoclonal antibodies or VEGF receptor immunofusions inhibit ocular neovascularization in both primate and rodent models. Regardless of the cause of induction of VEGF in human diabetic retinopathy, inhibition of ocular VEGF is useful in treating the disease.

Expression of VEGF is also significantly increased in hypoxic regions of animal and human tumors adjacent to areas of necrosis. VEGF is also upregulated by the expression of the oncogenes ras, raf, src and mutant p53 (all of which are relevant to targeting cancer). Monoclonal anti-VEGF antibodies inhibit the growth of human tumors in nude mice. Although these same tumor cells continue to express VEGF in culture, the antibodies do not diminish their mitotic rate. Thus tumor-derived VEGF does not function as an autocrine mitogenic factor. Therefore, VEGF contributes to tumor growth in vivo by promoting angiogenesis through its paracrine vascular endothelial cell chemotactic and mitogenic activities. These monoclonal antibodies also inhibit the growth of typically less well vascularized human colon cancers in athymic mice and decrease the number of tumors arising from inoculated cells.

Viral expression of a VEGF-binding construct of Flk-1, Flt-1, the mouse KDR receptor homologue, truncated to eliminate the cytoplasmic tyrosine kinase domains but retaining a membrane anchor, virtually abolishes the growth of a transplantable glioblastoma in mice presumably by the dominant negative mechanism of heterodimer formation with membrane spanning endothelial cell VEGF receptors. Embryonic stem cells, which normally grow as solid tumors in nude mice, do not produce detectable tumors if both VEGF alleles are knocked out. Taken together, these data indicate the role of VEGF in the growth of solid tumors. Inhibition of KDR or Flt-1 is implicated in pathological angiogenesis, and these receptors are useful in the treatment of diseases in which angiogenesis is part of the overall pathology, e.g., inflammation, diabetic retinal vascularization, as well as various forms of cancer since tumor growth is known to be dependent on angiogenesis. (Weidner et al., N. Engl. J. Med., 324, pp. 1–8, 1991).

Indolinyl-isoquinolinone compounds which specifically inhibit, regulate and/or modulate the signal transduction of tyrosine kinases have been previously reported, see WO 01/29025, published 26 Apr. 2001. The identification of compounds with improved pharmaceutical properties, however, remains desireable and is an object of this invention.

SUMMARY OF THE INVENTION

The present invention relates to compounds that are capable of inhibiting, modulating and/or regulating signal transduction of both receptor-type and non-receptor type tyrosine kinases. One embodiment of the present invention is illustrated by a compound of Formula I, and the pharmaceutically acceptable salts and stereoisomers thereof:

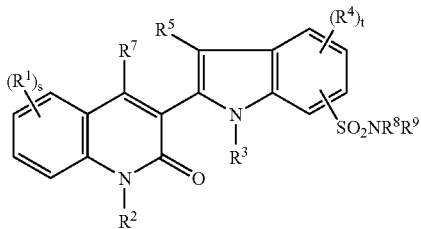

DETAILED DESCRIPTION OF THE INVENTION

The compounds of this invention are useful in the inhibition of kinases and are illustrated by a compound of Formula I:

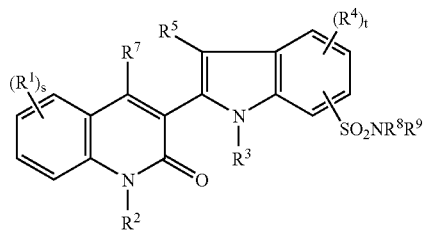

or a pharmaceutically acceptable salt or stereoisomer thereof, wherein
a is 0 or 1;
b is 0 or 1;
m is 0, 1, or 2;
s is 0,1 or 2;
t is 0,1 or 2;
$R^1$ and $R^4$ are independently:
   1) $(C=O)_aO_bC_1-C_{10}$ alkyl,
   2) $(C=O)_aO_b$aryl,
   3) $(C=O)_aO_bC_2-C_{10}$ alkenyl,
   4) $(C=O)_aO_bC_2-C_{10}$ alkynyl,
   5) $CO_2H$,
   6) halo,
   7) OH,
   8) $O_bC_1-C_6$ perfluoroalkyl,
   9) $(C=O)_aNR^8R^9$,
   10) CN,
   11) $SOmR^a$,
   12) $SO_mNR^8R^9$, or
   13) $(C=O)_aO_b$heterocyclyl, said alkyl, aryl, alkenyl, alkynyl, and heterocyclyl is optionally substituted with one or more substituents selected from $R^d$;
$R^2$ and $R^3$ are independently:
   1) H,
   2) $(C=O)O_aC_1-C_6$ alkyl, optionally substituted with aryl,
   3) $(C=O)O_a$aryl,
   4) $C_1-C_6$ alkyl, optionally substituted with aryl, or
   5) $SO_2R^a$;
$R^5$ and $R^7$ are independently H, halo, or $C_1-C_6$ alkyl;
$R^8$ and $R^9$ are independently:
   1) H,
   2) $(C=O)O_bC_1-C_{10}$ alkyl,
   3) $(C=O)O_b$aryl,
   4) $(C=O)O_b$heterocyclyl,
   5) $C_1-C_{10}$ alkyl,
   6) aryl,
   7) $C_2-C_{10}$ alkenyl,
   8) $C_2-C_{10}$ alkynyl,
   9) heterocyclyl,
   10) $SO_2R^a$,
   11) $(C=O)NR^b2$, or
   12) $C_1-C_{10}$ alkyl-$NR^b_2$, or $R^8$ and $R^9$ are taken together with the nitrogen to which they are attached to form a monocyclic or bicyclic heterocycle with 5–7 members in each ring and optionally containing, in addition to the nitrogen, one or two additional heteroatoms selected from N, O and S, said monocyclic or bicyclic heterocycle optionally substituted with one or more substituents selected from $R^c$;
Ra is $C_1-C_6$ alkyl, aryl, or benzyl;
$R^b$ is H, $C_1-C_6$ alkyl, aryl, or benzyl;

$R^c$ is:
1) $(C=O)_aO_b(C_1-C_{10})$alkyl, optionally substituted with $NR^b{}_2$,
2) oxo,
3) OH,
4) halo,
5) CN,
6) $SO_mR^a$,
7) aryl,
8) $NR^b{}_2$,
9) $C(O)R^a$,
10) $(C_0-C_6)$alkyl-$CO_2R^a$,
11) C(O)H, or
12) $(C_0-C_6)$alkyl-$CO_2H$; and $R^d$ is:
1) $(C=O)_aO_b(C_1-C_{10})$alkyl, optionally substituted with $NR^8R^9$,
2) oxo,
3) OH,
4) halo,
5) CN,
6) aryl,
7) $SO_mR^a$,
8) $NR^8R^9$,
9) $C(O)R^a$,
10) $(C_0-C_6)$alkyl-$CO_2R^a$,
11) C(O)H, or
12) $(C_0-C_6)$alkyl-$CO_2H$.

A second embodiment is a compound of Formula I as described above or a pharmaceutically acceptable salt or stereoisomer thereof, wherein s is 0 or 1;
t is 0 or 1;
$R^1$ and $R^4$ are independently:
1) $(C=O)_aO_bC_1-C_6$ alkyl,
2) $(C=O)_aO_b$aryl,
3) $(C=O)_aO_bC_2-C_6$ alkenyl,
4) $(C=O)_aO_bC_2-C_6$ alkynyl,
5) $CO_2H$,
6) halo,
7) OH,
8) $O_bC_1-C_6$ perfluoroalkyl,
9) $(C=O)_aNR^8R^9$, or
10) CN, said alkyl, aryl, alkenyl, and alkynyl is optionally substituted with one to three substituents selected from $R^d$;

$R^2$ and $R^3$ are independently:
1) H,
2) $(C=O)O_aC_1-C_3$ alkyl, optionally substituted with aryl,
3) $(C=O)O_a$aryl,
4) $C_1-C_3$ alkyl, optionally substituted with aryl, or
5) $SO_2R^a$;

$R^5$ and $R^7$ are independently H, halo, or $C_1-C_6$ alkyl;
$R^8$ and $R^9$ are independently:
1) H,
2) $(C=O)O_bC_1-C_6$ alkyl,
3) $(C=O)O_b$aryl,
4) $(C=O)O_b$heterocyclyl,
5) $C_1-C_6$ alkyl,
6) aryl,
7) $C_2-C_6$ alkenyl,
8) $C_2-C_8$ alkynyl,
9) heterocyclyl,
10) $SO_2R^a$,
11) $(C=O)NR^b2$, or
12) $C_1-C_6$ alkyl-$NR^b{}_2$, or $R^8$ and $R^9$ are taken together with the nitrogen to which they are attached to form a 5–7 membered heterocycle optionally containing, in addition to the nitrogen, one or two additional heteroatoms selected from N, O and S, and optionally substituted with one to three substituents selected from $R^c$;

$R^a$ is $C_1-C_6$ alkyl, aryl, or benzyl;
$R^b$ is H, $C_1-C_6$ alkyl, aryl, or benzyl;
$R^c$ is:
1) $(C=O)_aO_b(C_1-C_6)$alkyl, optionally substituted with $NR^b{}_2$,
2) oxo,
3) OH,
4) halo,
5) CN,
6) $SO_mR^a$,
7) aryl,
8) $NR^b{}_2$,
9) $C(O)R^a$,
10) $(C_0-C_6)$alkyl-$CO_2R^a$,
11) C(O)H, or
12) $(C_0-C_6)$alkyl-$CO_2H$; and $R^d$ is:
1) $(C=O)_aO_b(C_1-C_6)$alkyl, optionally substituted with $NR^8R^9$,
2) oxo,
3) OH,
4) halo,
5) CN,
6) aryl,
7) $SO_mR^a$,
8) $NR^8R^9$,
9) $C(O)R^a$,
10) $(C_0-C_6)$alkyl-$CO_2R^a$,
11) C(O)H, or
12) $(C_0-C_6)$alkyl-$CO_2H$.

A further embodiment is the compound of Formula I described immediately above or a pharmaceutically acceptable salt or stereoisomer thereof, wherein $R^1$ and $R^4$ are independently:
1) $(C=O)_aO_bC_1-C_6$ alkyl,
2) $(C=O)_aO_bC_2-C_6$ alkenyl,
3) $(C=O)_aO_bC_2-C_6$ alkynyl,
4) $CO_2H$,
5) halo,
6) OH, or
7) CN;

$R^2$ and $R^3$ are independently H or $C_1-C_3$ alkyl;
$R^5$ is H, $C_1-C_3$ alkyl or halogen;
$R^7$ is H;
$R^8$ and $R^9$ are independently:
1) H,
2) $(C=O)O_bC_1-C_6$ alkyl,
3) $(C=O)O_b$aryl,
4) $(C=O)O_b$heterocyclyl,
5) $C_1-C_6$ alkyl,
6) aryl,
7) $C_2-C_6$ alkenyl,
8) $C_2-C_8$ alkynyl,
9) heterocyclyl,
10) $SO_2R^a$,
11) $(C=O)NR^b2$, or
12) $C_0-C_6$ alkyl-$NR^b{}_2$, or $R^8$ and $R^9$ are taken together with the nitrogen to which they are attached to form a 5–7 membered heterocycle optionally containing, in addition to the nitrogen, one or two additional heteroatoms selected from N, O and S, and optionally substituted with one to three substituents selected from $R^c$;
$R^a$ is $C_1$–$C_6$ alkyl, aryl, or benzyl;
$R^b$ is H, $C_1$–$C_6$ alkyl, aryl, or benzyl;
$R^c$ is:
1) $(C=O)_aO_b(C_1$–$C_6)$alkyl, optionally substituted with $NR^b{}_2$,
2) oxo,
3) OH,
4) halo,
5) CN,
6) $SO_mR^a$,
7) aryl,
8) $NR^b{}_2$,
9) $C(O)R^a$,
10) $(C_0$–$C_6)$alkyl-$CO_2R^a$,
11) C(O)H, or
12) $(C_0$–$C_6)$alkyl-$CO_2H$; and
$R^d$ is:
1) $(C=O)_aO_b(C_1$–$C_6)$alkyl, optionally substituted with $NR^8R^9$,
2) oxo,
3) OH,
4) halo,
5) CN,
6) aryl,
7) $SO_mR^a$,
8) $NR^8R^9$,
9) $C(O)R^a$,
10) $(C_0$–$C_6)$alkyl-$CO_2R^a$,
11) C(O)H, or
12) $(C_0$–$C_6)$alkyl-$CO_2H$.

And yet another embodiment is a compound selected from:
3-{5-[(4-methylpiperazin-1-yl)sulfonyl]-1H-indol-2-yl}quinolin-2(1H)-one;
3-[5-(piperazin-1-ylsulfonyl)-1H-indol-2-yl]quinolin-2(1H)-one;
3-{5-[(3-aminopyrrolidin-1-yl)sulfonyl]-1H-indol-2-yl}quinolin-2(1H)-one;
N-[2-(dimethylamino)ethyl]-2-(2-oxo-1,2-dihydroquinolin-3-yl)-1H-indole-5-sulfonamide; and
N-methyl-2-(2-oxo-1,2-dihydroquinolin-3-yl)-N-pyrrolidin-3-yl-1H-indole-5-sulfonamide,
or a pharmaceutically acceptable salt or stereoisomer thereof.

Also included within the scope of the present invention is a pharmaceutical composition which is comprised of a compound of Formula I as described above and a pharmaceutically acceptable carrier.

Utilities

The compounds of the present invention are inhibitors of tyrosine kinase and are therefore useful to treat or prevent tyrosine kinase-dependent diseases or conditions in mammals.

"Tyrosine kinase-dependent diseases or conditions" refers to pathologic conditions that depend on the activity of one or more tyrosine kinases. Tyrosine kinases either directly or indirectly participate in the signal transduction pathways of a variety of cellular activities including proliferation, adhesion and migration, and differentiation. Diseases associated with tyrosine kinase activities include the proliferation of tumor cells, the pathologic neovascularization that supports solid tumor growth, ocular neovascularization (diabetic retinopathy, age-related macular degeneration, and the like) and inflammation (psoriasis, rheumatoid arthritis, and the like). In treating such conditions with the instantly claimed compounds, the required therapeutic amount will vary according to the specific disease and is readily ascertainable by those skilled in the art. Although both treatment and prevention are contemplated by the scope of the invention, the treatment of these conditions is the preferred use.

The present invention encompasses a method of treating or preventing cancer in a mammal in need of such treatment which is comprised of administering to said mammal a therapeutically effective amount of a claimed compound. Preferred cancers for treatment are selected from cancers of the brain, genitourinary tract, lymphatic system, stomach, larynx and lung. Another set of preferred forms of cancer are histiocytic lymphoma, lung adenocarcinoma, small cell lung cancers, pancreatic cancer, glioblastomas and breast carcinoma. A further preferred group of cancers for treatment with the present compounds is a cancers elected from lung cancer, prostate cancer, breast cancer and colorectal cancer. The utility of angiogenesis inhibitors in the treatment of cancer is known in the literature, see J. Rak et al. *Cancer Research*, 55:4575–4580, 1995, for example. The role of angiogenesis in cancer has been shown in numerous types of cancer and tissues: breast carcinoma (G. Gasparini and A. L. harris, *J. Clin. Oncol.*, 1995, 13:765–782; M. Toi et al., *Japan. J. Cancer Res.*, 1994, 85:1045–1049); bladder carcinomas (A. J. Dickinson et al., *Br. J. Urol.*, 1994, 74:762–766); colon carcinomas (L. M. Ellis et al., Surgery, 1996, 120(5):871–878); and oral cavity tumors (J. K. Williams et al., *Am. J. Surg.*, 1994, 168:373–380).

Tumors which have undergone neovascularization show an increased potential for metastasis. VEGF released from cancer cells enhances metastasis possibly by increasing extravasation at points of adhesion to vascular endothelium. (A. Amirkhosravi et al., *Platelets*, 10:285–292 (1999)). In fact, angiogenesis is essential for tumor growth and metastasis. (S. P. gunningham, et al., *Can. Research*, 61: 3206–3211 (2001)). The angiogenesis inhibitors disclosed in the present application are therefore also useful to prevent or decrease tumor cell metastasis. Such a use is also contemplated to be within the scope of the present invention.

Further included within the scope of the invention is a method of treating or preventing a disease in which angiogenesis is implicated, which is comprised of administering to a mammal in need of such treatment a therapeutically effective amount of a compound of the present invention. Ocular neovascular diseases are an example of conditions where much of the resulting tissue damage can be attributed to aberrant infiltration of blood vessels in the eye (see WO 00/30651, published 2 Jun. 2000). The undesireable infiltration can be triggered by ischemic retinopathy, such as that resulting from diabetic retinopathy, retinopathy of prematurity, retinal vein occlusions, etc., or by degenerative diseases, such as the choroidal neovascularization observed in age-related macular degeneration. Inhibiting the growth of blood vessels by administration of the present compounds would therefore prevent the infiltration of blood vessels and prevent or treat diseases where angiogenesis is implicated, such as ocular diseases like retinal vascularization, diabetic retinopathy, age-related macular degeneration, and the like.

Also included within the scope of the present invention is a method of treating or preventing inflammatory diseases which comprises administering to a mammal in need of such treatment a therapeutically effective amount of a compound of Formual I. Examples of such inflammatory diseases are rheumatoid arthritis, psoriasis, contact dermatitis, delayed hypersensitivity reactions, and the like. (A. Giatromanolaki et al., *J. Pathol.* 2001; 194:101–108.) For the role of VEGF in skin angiogenesis, see Michael Detmar, J. *Dermatological Sci.*, 24 Suppl. 1, S78–S84 (2000).

Also included within the scope of the present invention is a method of treating or preventing bone associated pathologies selected from osteosarcoma, osteoarthritis, and rickets, also known as oncogenic osteomalacia. (Hasegawa et al., *Skeletal Radiol.*, 28, pp.41–45, 1999; Gerber et al., *Nature Medicine*, Vol. 5, No. 6, pp.623–628, June 1999.) And since VEGF directly promotes osteoclastic bone resorption through KDR/Flk-1 expressed in mature osteoclasts (FEBS Let. 473:161–164 (2000); *Endocrinology*, 141:1667 (2000)), the instant compounds are also useful to treat and prevent conditions related to bone resorption, such as osteoporosis and Paget's disease.

A method of treating or preventing preeclampsia is also within the scope of the present invention, which comprises administering a therapeutically effective amount of a compound of Formula I. Studies have shown that the action of VEGF on the Flt-1 receptor is pivotal in the pathogenesis of preeclampsia. (*Laboratory Investigation* 79:1101–1111 (September 1999).) Vessels of pregnant women incubated with VEGF exhibit a reduction in endothelium-dependent relaxation similar to that induced by plasma from women with preeclampsia. In the presence of an anti-Flt-1 receptor antibody, however, neither VEGF or plasma from women with preeclampsia reduced the endothelium-dependent relaxation. Therefore the claimed compounds serve to treat preeclampsia via their action on the tyrosine kinase domain of the Flt-1 receptor.

Also within the scope of the invention is a method of reducing or preventing tissue damage following a cerebral ischemic event which comprises administering a therapeutically effective amount of a compound of the present invention. The claimed compounds can also be used to reduce or prevent tissue damage which occurs after cerebral ischemic events, such as stroke, by reducing cerebral edema, tissue damage, and reperfusion injury following ischemia. (*Drug News Perspect* 11:265–270 (1998); *J. Clin. Invest.* 104:1613–1620 (1999); *Nature Med.* 7:222–227 (2001)).

The instant compounds can also be used to prevent or treat tissue damage during bacterial meningitis, such as tuberculous meningitis. (Matsuyama et al., *J. Neurol. Sci.* 186: 75–79 (2001)). The instant invention therefore encompasses a method of treating or preventing tissue damage due to bacterial meningitis which comprises administering a therapeutically effective amount of a claimed compound. Studies have shown that VEGF is secreted by inflammatory cells during bacterial meningitis and that VEGF contributes to blood-brain barrier disruption. (van der Flier et al., *J. Infectious Diseases*, 183:149–153 (2001)). The claimed compounds can inhibit VEGF-induced vascular permeability and therefore serve to prevent or treat blood-brain barrier disruption associated with bacterial meningitis.

The present invention further encompasses a method to treat or prevent endometriosis comprised of administering a therapeutically effective amount of a claimed compound. An increase in VEGF expression and angiogenesis is associated with the progression of endometriosis (Stephen K. Smith, *Trends in Endocrinology & Metabolism*, Vol. 12, No. 4, May/June 2001). Inhibition of VEGF by the current compounds would therefore inhibit angiogenesis and treat endometriosis.

A further embodiment of the present invention is a method of treating acute myeloid leukemia (AML) which comprises administering a therapeutically effective amount of a claimed compound. Activation of FLT3 on leukemic cells by FLT3 ligand leads to receptor dimerization and signal transduction in pathways that promote cell growth and inhibit apoptosis (*Blood*, Vol. 98, No. 3, pp.885–887 (2001)). The present compounds are therefore useful to treat AML via inhibition of the tyrosine kinase domain of Flt-3.

The disclosed compounds are also useful in the treatment of hyper-tension. Studies have shown the VEGF and sFlt-1 levels are significantly raised in patients with uncomplicated essential hypertension. The elevated plasma levels of VEGF and sFlt-1 lead to abnormal angiogenesis which contributes to endothelial cell dysfunction in hypertension. Since the abnormal angiogenesis contributes casually to hypertension, treatment with angiogenesis inhibitors would ameliorate the complications due to hypertension. (see *J. Hyperts.*, 1998; 16:1563–1572; and *Amer. J. Cardiology*, Vol. 87, pp.805–807 (Mar. 15, 2001)).

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The instant compounds are also useful in combination with known anti-cancer agents. Combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors. The instant compounds are particularly useful when coadminsitered with radiation therapy. The synergistic effects of inhibiting VEGF in combination with radiation therapy have been described in the art (see WO 00/61186). The use of angiogenesis inhibitors with other chemotherapeutic agents is especially desirable since the normalization of tumor vasculature improves the delivery of the other therapeutic agents. (Nature Medicine, Vol. 7. No. 9, pp. 987–989 (September 2001)).

"strogen receptor modulators" refers to compounds which interfere or inhibit the binding of estrogen to the receptor, regardless of mechanism. Examples of estrogen receptor modulators include, but are not limited to, tamoxifen, raloxifene, idoxifene, LY35338 1, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, a-difluoromethylornithine, ILX23-7553, trans-N-(4'-hydroxyphenyl) retinamide, and N-4-carboxyphenyl retinamide.

"Cytotoxic agents" refer to compounds which cause cell death primarily by interfering directly with the cell's functioning or inhibit or interfere with cell myosis, including alkylating agents, tumor necrosis factors, intercalators, microtubulin inhibitors, and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine) platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, N,N-dimethyl-L-valyl-L-valyl-N-methyl-L-valyl-L-prolyl-L-proline-t-butylamide, TDX258, and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H, 12H-benzo[de]pyrano[3',4':b,7]indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino]benzo[g]isoquinolinone-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen4-ylmethyl] formamide, N-(2-(dimethyl amino)ethyl) acridine-4-carboxamide, 6-[[2-(dimethylamino)ethyl]amino]-3-hydroxy-7H-indeno[2,1-c] quinolin-7-one, and dimesna.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluidine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl) urea, N6-[4-deoxy4[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab, and tumor suppressor genes, such as p53, which can be delivered via recombinant virus-mediated gene transfer (see U.S. Pat. No. 6,069,134, for example).

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. 4,231,938 at col. 6, and WO 84/02131 at pp. 30–33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85–89 (5 Feb. 1996) and U.S. Pat. Nos. 4,782,084 and 4,885,314. The term HMG- CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

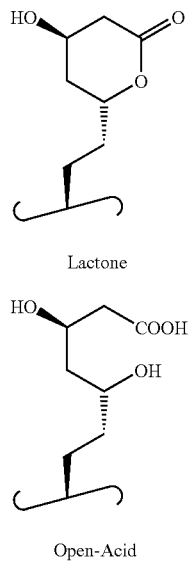

Lactone

Open-Acid

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'yl-methylbenzimidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl)methyl]4-(3-chlorophenyl)-1-methyl-2(1H)-quinolinone, (−)-6-[amino(4-chlorophenyl)(1-methyl-1H-imidazol-5-yl)methyl]-4-(3-chlorophenyl)-1-methyl-2(1H)-quinolinone, (+)-6-[amino(4-chlorophenyl)(1-methyl-1H-imidazol-5-yl)methyl]-4-(3-chlorophenyl)-1-methyl-2(1H)-quinolinone, 5(S)-n-butyl-1-(2,3-dimethylphenyl)-4-[1-(4-cyanobenzyl)-5-imidazolylmethyl]-2-piperazinone, (S)-1-(3-chlorophenyl)-4-[1-(4-cyanobenzyl)-5-imidazolylmethyl]-5-[2-(ethanesulfonyl) methyl]-2-piperazinone, 5(S)-n-Butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{5-[4-hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2']bipyridin-5'-ylmethyl]-3H-imidazol-4-ylmethyl}benzonitrile, 4-{3-[4-(2-oxo-2H-[1,2']bipyridin-5'-ylmethyl]-3H-imidazol-4-ylmethyl}benzonitrile, 4-[3-(2-oxo-1-phenyl-1,2-dihydropyridin-4-ylmethyl)-3H-imidazol-4-ylmethyl}benzonitrile, 18,19-dihydro-19-oxo-5H,17H-6,10:12,16-dimetheno-1H-imidazo[4,3-c][1,11,4] dioxaazacyclononadecine-9-carbonitrile, (±)-19,20-dihydro-19-oxo-5H-18,21-ethano-12,14-etheno-6,10-metheno-22H-benzo[d]imidazo[4,3-k][1,6,9,12]oxatriazacyclooctadecine-9-carbonitrile, 19,20-dihydro-19-oxo-5H,17H-18,21-ethano-6,10:12,16-diretheno-22H-imidazo[3,4-h][1,8,11,14]oxatriazacycloeicosine-9-carbonitrile, and (±)-19,20-dihydro-3-methyl-19-oxo-5H-18,21-ethano-12,14-etheno-6,10-metheno-22H-benzo [d]imidazo[4,3-k][1,6,9,12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp.1394–1401 (1999).

Examples of HIV protease inhibitors include amprenavir, abacavir, CGP-73547, CGP-61755, DMP450, indinavir, nelfinavir, tipranavir, ritonavir, saquinavir, ABT-378, AG 1776, and BMS-232,632. Examples of reverse transcriptase inhibitors include delaviridine, efavirenz, GS-840, HB Y097, lamivudine, nevirapine, AZT, 3TC, ddC, and ddI.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR20), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p.573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p.107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141–145 (1985)), and antibodies to VEGF (see, Nature Biotechnology, Vol. 17, pp.963–968 (October 1999); Kim et al., Nature, 362, 841–844 (1993); WO 00/44777; and WO 00/61186).

As described above, the combinations with NSAID's are directed to the use of NSAID's which are potent COX-2 inhibiting agents. For purposes of this specification an NSAID is potent if it possess an $IC_{50}$ for the inhibition of COX-2 of 1 μM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat No. 5,698,584, issued Dec. 16, 1997, U.S. Pat. No. 5,710,140, issued Jan. 20,1998, WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999, all of which are hereby incorporated by reference.

Inhibitors of COX-2 that are particularly useful in the instant method of treatment are:

3-phenyl-4-(4-(methylsulfonyl)phenyl)-2-(5H)-furanone; and

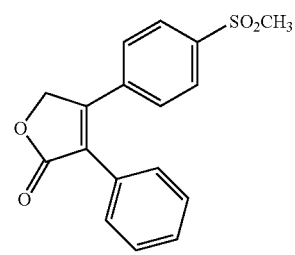

5-chloro-3-(4-methylsulfonyl)phenyl-2-(2-methyl-5-pyridinyl)pyridine;

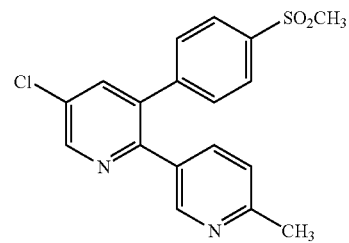

or a pharmaceutically acceptable salt thereof.

General and specific synthetic procedures for the preparation of the COX-2 inhibitor compounds described above are found in U.S. Pat. No. 5,474,995, issued Dec. 12, 1995, U.S. Pat. No. 5,861,419, issued Jan. 19, 1999, and U.S. Pat. No. 6,001,843, issued Dec. 14, 1999, all of which are herein incorporated by reference.

Compounds that have been described as specific inhibitors of COX-2 and are therefore useful in the present invention include, but are not limited to, the following:

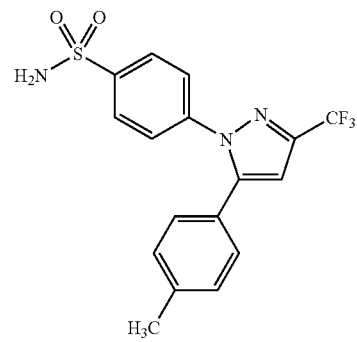

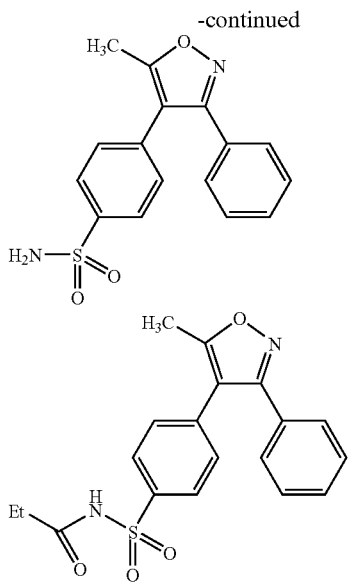

or a pharmaceutically acceptable salt thereof.

Compounds which are described as specific inhibitors of COX-2 and are therefore useful in the present invention, and methods of synthesis thereof, can be found in the following patents, pending applications and publications, which are herein incorporated by reference: WO 94/15932, published Jul. 21,1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999.

Compounds which are specific inhibitors of COX-2 and are therefore useful in the present invention, and methods of synthesis thereof, can be found in the following patents, pending applications and publications, which are herein incorporated by reference: U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604,260, issued Feb. 18, 1997, U.S. Pat. No. 5,698,584, issued Dec. 16, 1997, and U.S. Pat. No. 5,710,140, issued Jan. 20, 1998.

Other examples of angiogenesis inhibitors include, but are not limited to, endostation, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonyl-imino [N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counter-act binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$,$\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo [2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI1571A, N-4-chlorophenyl-4(4-pyridylmethyl)-1-phthalazinamine, and EMD121974.

The instant compounds are also useful, alone or in combination with platelet fibrinogen receptor (GP IIb/IIIa) antagonists, such as tirofiban, to inhibit metastasis of cancerous cells. Tumor cells can activate platelets largely via thrombin generation. This activation is associated with the release of VEGF. The release of VEGF enhances metastasis by increasing extravasation at points of adhesion to vascular endothelium (Amirkhosravi, *Platelets* 10, 285–292, 1999). Therefore, the present compounds can serve to inhibit metastasis, alone or in combination with GP IIb/IIIa antagonists. Examples of other fibrinogen receptor antagonists include abciximab, eptifibatide, sibrafiban, lamifiban, lotrafiban, cromofiban, and CT50352.

Combinations with compounds other than anti-cancer compounds are also encompassed to treat conditions other than cancer. For example, combinations of the instantly claimed compounds with PPAR-γ (i.e., PPAR-gamma) agonists are useful in the treatment of diabetic retinopathy. PPAR-γ is the nuclear peroxisome proliferator-activated receptor γ. The expression of PPAR-γ on endothelial cells and its involvement in angiogenesis in corneal and choroidal experimental systems has been reported in the literature (see *J. Cardiovasc. Pharmacol.* 1998; 31:909–913; *J. Biol. Chem.* 1999;274:9116–9121; *Invest. Ophthalmol Vis. Sci.* 2000; 41:2309–2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709–717). Examples of PPAR-γ aganoists and PPAR-γ/α aganoists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. Nos. 60/235,708 and 60/244,697). Thus, a method of treating or preventing diabetic retinopathy which comprises administering a therapeutically effective amount of a claimed compound in combination with a PPAR-γ agonist is also within the scope of the present invention.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The scope of the invention therefore encompasses the use of the instantly claimed compounds in combination with a second compound selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

Preferred angiogenesis inhibitors to be used as the second compound are a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamido-triazole, combretastatin A-4, squalamine, 6-O-(chloroacetyl-carbonyl)-fumagillol, thalidomide, angiostatin, troponin-1, or an antibody to VEGF. Preferred estrogen receptor modulators are tamoxifen and raloxifene.

Also included in the scope of the claims is a method of treating cancer which comprises administering a therapeutically effective amount of a claimed compound in combination with radiation therapy and/or in combination with a compound selected from:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) another angiogenesis inhibitor.

And yet another embodiment of the invention is a method of treating cancer which comprises administering a therapeutically effective amount of a compound of Formual I in combination with paclitaxel or trastuzumab.

The invention further encompasses a method of treating or preventing cancer which comprises administering a therapeutically effective amount of a claimed compound in combination with a COX-2 inhibitor.

These and other aspects of the invention will be apparent from the teachings contained herein.

The compounds of the present invention may have asymmetric centers, chiral axes, and chiral planes (as described in: E. L. Eliel and S. H. Wilen, *Stereo-chemistry of Carbon Compounds*, John Wiley & Sons, New York, 1994, pages 1119–1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

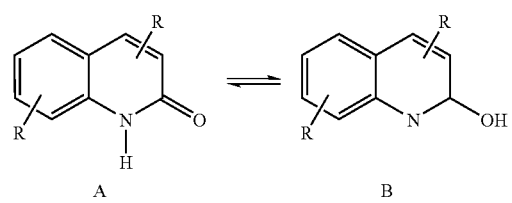

A          B

When any variable (e.g. $R^4$, $R^6$, $R^{6a}$, etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched and unbranched, cyclic and acyclic saturated aliphatic hydrocarbon groups having the specified number of carbon atoms. For example, $C_1$–$C_{10}$, as in "$C_1$–$C_{10}$alkyl" is defined to include groups having 1, 2, 3, 4, 5, 6, 7, 8, 9 or 10 carbons in a linear or branched arrangement and may be cyclic or acyclic. For example, "$C_1$–$C_{10}$ alkyl" specifically includes methyl, ethyl, n-propyl, i-propyl, n-butyl, t-butyl, i-butyl, pentyl, hexyl, heptyl, octyl, nonyl, decyl, cyclopropyl, methyl-cyclopropyl, 2,2-dimethyl-cyclobutyl, 2-ethyl-cyclopentyl, cyclohexyl, and so on and so on.

"Alkoxy" represents an alkyl group of indicated number of carbon atoms as defined above attached through an oxygen bridge.

If no number of carbon atoms is specified, the term "alkenyl" refers to a non-aromatic hydrocarbon radical, which may be branched or unbranched and cyclic or acyclic, containing from 2 to 10 carbon atoms and at least one carbon to carbon double bond. Preferably one carbon to carbon double bond is present, and up to four non-aromatic carbon-carbon double bonds may be present. Thus, "$C_2$–$C_6$ alkenyl" means an alkenyl radical having from 2 to 6 carbon atoms. Alkenyl groups include ethenyl, propenyl, butenyl, 2-methylbutenyl, cyclohexenyl, methylenylcyclohexenyl, and so on.

The term "alkynyl" refers to a hydrocarbon radical, which may be branched or unbranched and cyclic or acyclic, containing from 2 to 10 carbon atoms and at least one carbon to carbon triple bond. Up to three carbon-carbon triple bonds may be present. Thus, "$C_2$–$C_6$ alkynyl" means an alkynyl radical having from 2 to 6 carbon atoms. Alkynyl groups include ethynyl, propynyl, butynyl, 3-methylbutynyl and so on.

In certain instances, substituents may be defined with a range of carbons that includes zero, such as ($C_0$–$C_6$)alkylene-aryl. If aryl is taken to be phenyl, this definition would include phenyl itself as well as —$CH_2Ph$, —$CH_2CH_2Ph$, $CH(CH_3)CH_2CH(CH_3)Ph$, and so on.

As used herein, "aryl" is intended to mean phenyl and substituted phenyl, including moieties with a fused benzo group. Examples of such aryl elements include phenyl, naphthyl, tetrahydronaphthyl, indanyl, biphenyl, phenanthryl, anthryl or acenaphthyl. In cases where the aryl substituent is bicyclic, it is understood that attachment is via the phenyl ring. Unless otherwise indicated, "aryl" includes phenyls substituted with one or more substituents.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

As appreciated by those of skill in the art, "halo" or "halogen" as used herein is intended to include chloro, fluoro, bromo and iodo.

The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrahydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

The alkyl, alkenyl, alkynyl, cycloalkyl, aryl, heteroaryl and heterocyclyl substituents may be unsubstituted or unsubstituted, unless specifically defined otherwise. For example, a ($C_1$–$C_6$)alkyl may be substituted with one, two or three substituents selected from OH, oxo, halogen, alkoxy, dialkylamino, or heterocyclyl, such as morpholinyl, piperidinyl, and so on. In this case, if one substituent is oxo and the other is OH, the following are included in the definition: —C(=O)$CH_2$CH(OH)$CH_3$, —(C=O)OH, —$CH_2$(OH)$CH_2$CH(O), and so on.

The pharmaceutically acceptable salts of the compounds of this invention include the conventional non-toxic salts of the compounds of this invention as formed inorganic or organic acids. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. The preparation of the pharmaceutically acceptable salts described above and other typical pharmaceutically acceptable salts is more fully described by Berg et al., "Pharmaceutical Salts," *J. Pharm. Sci.*, 1977:66:1–19, hereby incorporated by reference.

In certain instances, $R^7$ and $R^8$ are defined such that they can be taken together with the nitrogen to which they are attached to form a monocyclic or bicyclic heterocycle with 5–7 members in each ring and optionally containing, in addition to the nitrogen, one or two additional heteroatoms selected from N, O and S, said heterocycle optionally substituted with one or more substituents selected from $R^{6a}$. Examples of the heterocycles that can thus be formed include, but are not limited to the following, keeping in mind that the heterocycle is optionally substituted with one or more substituents chosen from $R^{6a}$:

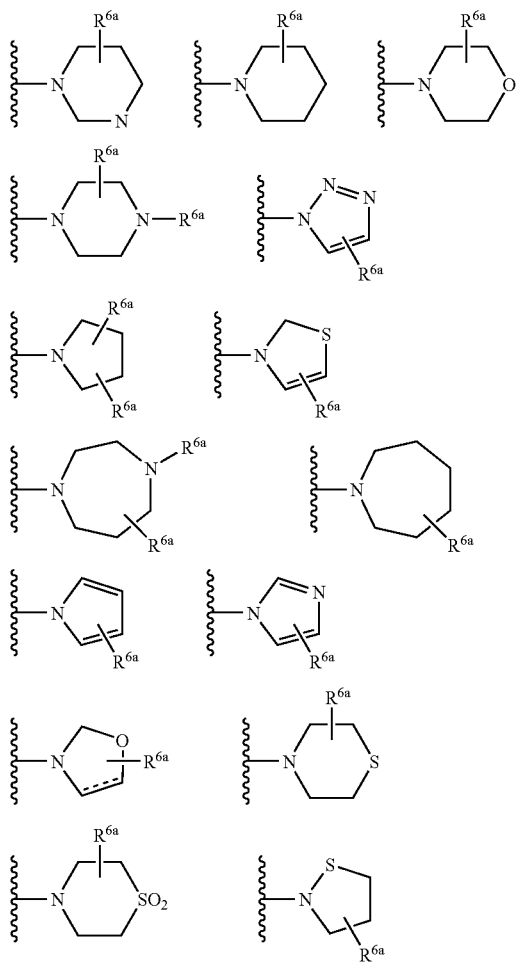

-continued

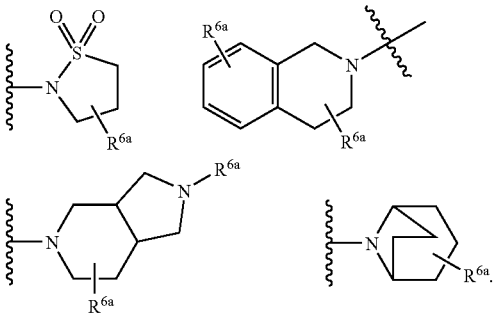

Preferably $R^1$ is H or halogen. Most preferably $R^1$ is H.

Also preferred is the definition of $R^2$ and $R^3$ as H.

Preferably $R^5$ is halogen or H. More preferably $R^5$ is H or F. Most preferably $R^5$ is H.

The preferred heterocyclyl substituents are those shown immediately above plus pyridine, pyrrolidine, pyrazine, pyridazine, tetramethylenesulfone, butyrolactone, tetrahydrofuran, furan, indole, and thiophene.

Preferably t is 0 or 1. Most preferably t is 0.

Preferably $R^7$ and $R^8$ are defined such that they are be taken together with the nitrogen to which they are attached to form a monocyclic 5–7 membered heterocycle and optionally containing, in addition to the nitrogen, one or two additional heteroatoms selected from N, O and S, and said heterocycle optionally substituted with one or more substituents selected from $R^{6a}$.

The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The compounds of this invention may be prepared by employing reactions as shown in the following schemes, in addition to other standard manipulations that are known in the literature or exemplified in the experimental procedures. These schemes, therefore, are not limited by the compounds listed or by any particular substituents employed for illustrative purposes. Substituent numbering as shown in the schemes does not necessarily correlate to that used in the claims.

Schemes

The compounds of the instant invention can be prepared by following the genralized procdure shown in Schemes A and B. Although the synthesis of one isomer is exempliﬁed in Scehem B, the same sequence can be used by the skilled artisan to prepare the different regioisomers. As shown in Scheme C, the compounds can be selectively flourinated on the indole by the use of appropriate reagents and conditions.

SCHEME A
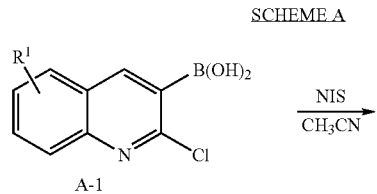
A-1
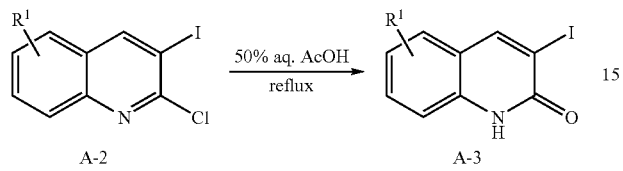
A-2        A-3
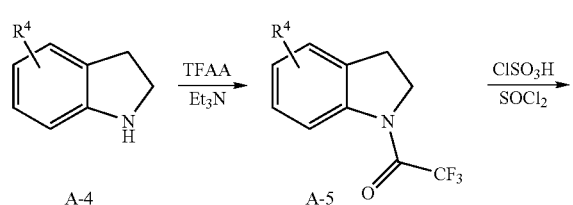
A-4        A-5
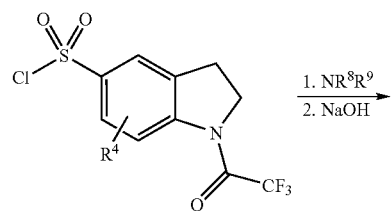
A-6
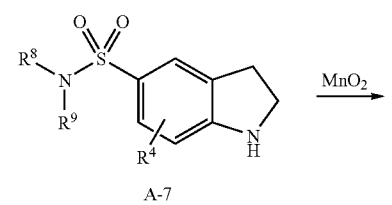
A-7
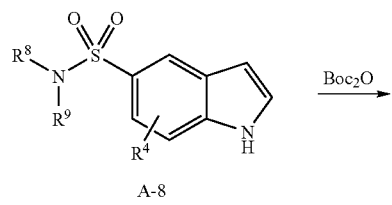
A-8
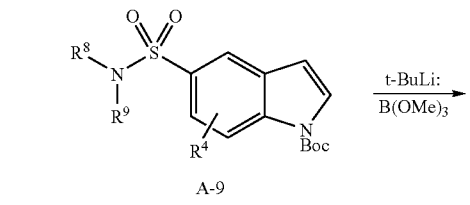
A-9
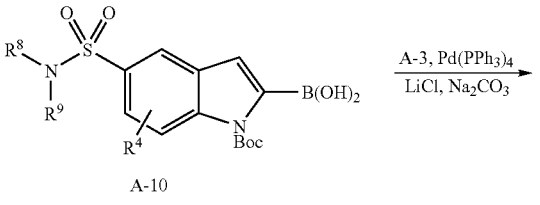
A-10
-continued
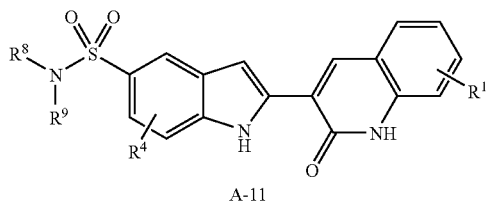
A-11
SCHEME B
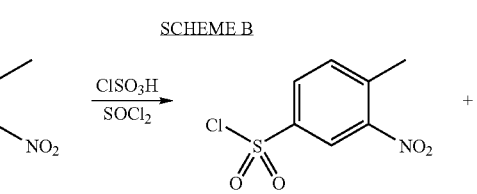
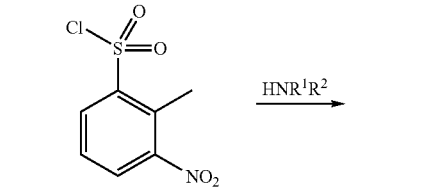
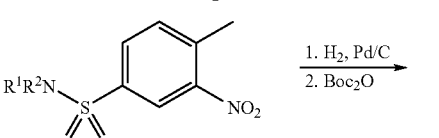
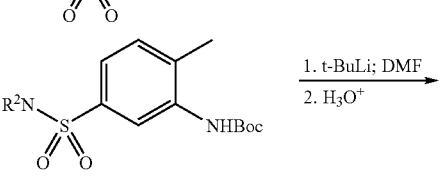
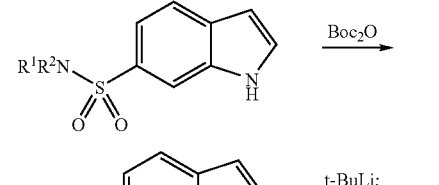
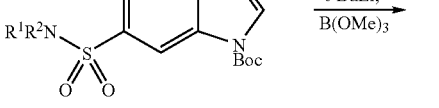
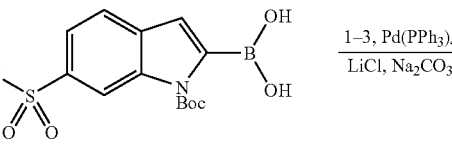
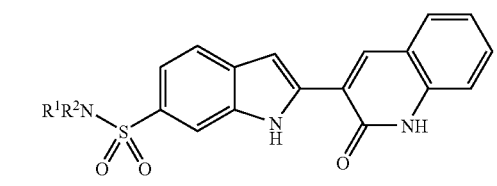

SCHEME C

[Structure C-1: R¹R²N-sulfonyl-indole linked to quinolinone NH]

Selectfluor™ →

[Structure C-2: fluorinated product]

Assays

The compounds of the instant invention described in the Examples were tested by the assays described below and were found to have kinase inhibitory activity. Other assays are known in the literature and could be readily performed by those of skill in the art (see, for example, Dhanabal et al., *Cancer Res.* 59:189–197; Xin et al., *J. Biol. Chem.* 274: 9116–9121; Sheu et al., *Anticancer Res.* 18:4435–4441; Ausprunk et al., *Dev. Biol.* 38:237–248; Gimbrone et al., *J. Natl. Cancer Inst.* 52:413–427; Nicosia et al., *In Vitro* 18:538–549).

I. VEGF Receptor Kinase Assay

VEGF receptor kinase activity is measured by incorporation of radio-labeled phosphate into polyglutamic acid, tyrosine, 4:1 (pEY) substrate. The phosphorylated pEY product is trapped onto a filter membrane and the incorporation of radio-labeled phosphate quantified by scintillation counting.

Materials

VEGF Receptor Kinase

The intracellular tyrosine kinase domains of human KDR (Terman, B. I. et al. Oncogene (1991) vol. 6, pp. 1677–1683.) and Flt-1 (Shibuya, M. et al. Oncogene (1990) vol. 5, pp. 519–524) were cloned as glutathione S-transferase (GST) gene fusion proteins. This was accomplished by cloning the cytoplasmic domain of the KDR kinase as an in frame fusion at the carboxy terminus of the GST gene. Soluble recombinant GST-kinase domain fusion proteins were expressed in Spodoptera frugiperda (Sf21) insect cells (Invitrogen) using a baculovirus expression vector (pAcG2T, Pharmingen).

The other materials used and their compositions were as follows:

Lysis buffer: 50 mM Tris pH 7.4, 0.5 M NaCl, 5 mM DTT, 1 mM EDTA, 0.5% triton X-100, 10% glycerol, 10 mg/mL of each leupeptin, pepstatin and aprotinin and 1 mM phenylmethylsulfonyl fluoride (all Sigma).

Wash buffer: 50 mM Tris pH 7.4,0.5 M NaCl, 5 mM DTT, 1 mM EDTA, 0.05% triton X-100, 10% glycerol, 10 mg/mL of each leupeptin, pepstatin and aprotinin and 1 mM phenylmethylsulfonyl fluoride.

Dialysis buffer: 50 mM Tris pH 7.4,0.5 M NaCl, 5 mM DTT, 1 mM EDTA, 0.05% triton X-100, 50% glycerol, 10 mg/mL of each leupeptin, pepstatin and aprotinin and 1 mM phenylmethylsulfonyl fluoride.

10× reaction buffer: 200 mM Tris, pH 7.4, 1.0 M NaCl, 50 mM $MnCl_2$, 10 mM DTT and 5 mg/mL bovine serum albumin (Sigma).

Enzyme dilution buffer: 50 mM Tris, pH 7.4, 0.1 M NaCl, 1 mM DTT, 10% glycerol, 100 mg/mL BSA.

10× Substrate: 750 µg/mL poly (glutamic acid, tyrosine; 4:1) (Sigma).

Stop solution: 30% trichloroacetic acid, 0.2 M sodium pyrophosphate (both Fisher).

Wash solution: 15% trichloroacetic acid, 0.2 M sodium pyrophosphate.

Filter plates: Millipore #MAFC NOB, GF/C glass fiber 96 well plate.

Method

A. Protein Purification

1. Sf21 cells were infected with recombinant virus at a multiplicity of infection of 5 virus particles/cell and grown at 27° C. for 48 hours.

2. All steps were performed at 4° C. Infected cells were harvested by centrifugation at 1000×g and lysed at 4° C. for 30 minutes with 1/10 volume of lysis buffer followed by centrifugation at 100,000×g for 1 hour. The supernatant was then passed over a glutathione Sepharose column (Pharmacia) equilibrated in lysis buffer and washed with 5 volumes of the same buffer followed by 5 volumes of wash buffer. Recombinant GST-KDR protein was eluted with wash buffer/10 mM reduced glutathione (Sigma) and dialyzed against dialysis buffer.

B. VEGF Receptor Kinase Assay

1. Add 5 µl of inhibitor or control to the assay in 50% DMSO.

2. Add 35 µl of reaction mix containing 5 µl of 10× reaction buffer, 5 µl 25 mM ATP/10 µCi [$^{33}$P]ATP (Amersham), and 5 µl 10× substrate.

3. Start the reaction by the addition of 10 µl of KDR (25 nM) in enzyme dilution buffer.

4. Mix and incubate at room temperature for 15 minutes.

5. Stop by the addition of 50 µl stop solution.

6. Incubate for 15 minutes at 4° C.

7. Transfer a 90 µl aliquot to filter plate.

8. Aspirate and wash 3 times with wash solution.

9. Add 30 µl of scintillation cocktail, seal plate and count in a Wallac Microbeta scintillation counter.

II. Human Umbilical Vein Endothelial Cell Mitogenesis Assay

Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (bFGF). The mitogenic response to VEGF or bFGF is determined by measuring the incorporation of [$^3$H]thymidine into cellular DNA.

Materials

HUVECs: HUVECs frozen as primary culture isolates are obtained from Clonetics Corp. Cells are maintained in Endothelial Growth Medium (EGM; Clonetics) and are used for mitogenic assays described in passages 1–5 below.

Culture Plates: NUNCLON 96-well polystyrene tissue culture plates (NUNC #167008).

Assay Medium: Dulbecco's. modification of Eagle's medium containing 1 mg/mL glucose (low-glucose DMEM; Mediatech) plus 10% (v/v) fetal bovine serum (Clonetics).

Test Compounds: Working stocks of test compounds are diluted serially in 100% dimethylsulfoxide (DMSO) to 400-fold greater than their desired final concentrations. Final dilutions to 1× concentration are made directly into Assay Medium immediately prior to addition to cells.

10× Growth Factors: Solutions of human $VEGF_{165}$ (500 ng/mL; R&D Systems) and bFGF (10 ng/mL; R&D Systems) are prepared in Assay Medium.

10× [$^3$H]thymidine: [Methyl-$^3$H]thymidine (20 Ci/mmol; Dupont-NEN) is diluted to 80 μCi/mL in low-glucose DMEM.

Cell Wash Medium: Hank's balanced salt solution (Mediatech) containing 1 mg/mL bovine serum albumin (Boehringer-Mannheim).

Cell Lysis Solution: 1 N NaOH, 2% (w/v) $Na_2CO_3$.

Method

1. HUVEC monolayers maintained in EGM are harvested by trypsinization and plated at a density of 4000 cells per 100 μL Assay Medium per well in 96-well plates. Cells are growth-arrested for 24 hours at 37° C. in a humidified atmosphere containing 5% $CO_2$.

2. Growth-arrest medium is replaced by 100 μL Assay Medium containing either vehicle (0.25% [v/v] DMSO) or the desired final concentration of test compound. All determinations are performed in triplicate. Cells are then incubated at 37° C. with 5% $CO_2$ for 2 hours to allow test compounds to enter cells.

3. After the 2-hour pretreatment period, cells are stimulated by addition of 10 μL/well of either Assay Medium, 10× VEGF solution or 10× bFGF solution. Cells are then incubated at 37° C. and 5% $CO_2$.

4. After 24 hours in the presence of growth factors, 10× [$^3$H]thymidine (10 μL/well) is added.

5. Three days after addition of [$^3$H]thymidine, medium is removed by aspiration, and cells are washed twice with Cell Wash Medium (400 μL/well followed by 200 μL/well). The washed, adherent cells are then solubilized by addition of Cell Lysis Solution (100 μL/well) and warming to 37° C. for 30 minutes. Cell lysates are transferred to 7-mL glass scintillation vials containing 150 μL of water. Scintillation cocktail (5 mL/vial) is added, and cell-associated radioactivity is determined by liquid scintillation spectroscopy.

Based upon the foregoing assays the compounds of the present invention are inhibitors of VEGF and thus are useful for the inhibition of angiogenesis, such as in the treatment of ocular disease, e.g., diabetic retinopathy and in the treatment of cancers, e.g., solid tumors. The instant compounds inhibit VEGF-stimulated mitogenesis of human vascular endothelial cells in culture with $IC_{50}$ values between 0.01–5.0 μM. These compounds may also show selectivity over related tyrosine kinases (e.g., FGFR1 and the Src family; for relationship between Src kinases and VEGFR kinases, see Eliceiri et al., Molecular Cell, Vol. 4, pp.915–924, December 1999).

III. FLT-1 Kinase Assay

Flt-1 was expressed as a GST fusion to the Flt-1 kinase domain and was expressed in baculovirus/insect cells. The following protocol was employed to assay compounds for Flt-1 kinase inhibitory activity:

1. Inhibitors were diluted to account for the final dilution in the assay, 1:20.
2. The appropriate amount of reaction mix was prepared at room temperature:
    10× Buffer (20 mM Tris pH 7.4/0.1 M NaCl/1 mM DTT final)
    0.1M $MnCl_2$ (5 mM final)
    pEY substrate (75 μg/mL)
    ATP/[$^{33}$P]ATP (2.5 μM/1 μCi final)
    BSA (500 μg/mL final).
3. 5 μL of the diluted inhibitor was added to the reaction mix. (Final volume of 5 μL in 50% DMSO). To the positive control wells, blank DMSO (50%) was added.
4. 35 μL of the reaction mix was added to each well of a 96 well plate.
5. Enzyme was diluted into enzyme dilution buffer (kept at 4° C.).
6. 10 μL of the diluted enzyme was added to each well and mix (5 nM final). To the negative control wells, 10 μL 0.5 M EDTA was added per well instead (final 100 mM).
7. Incubation was then carried out at room temperature for 30 minutes.
8. Stopped by the addition of an equal volume (50 μL) of 30% TCA/0.1M Na pyrophosphate.
9. Incubation was then carried out for 15 minutes to allow precipitation.
10. Transfered to Millipore filter plate.
11. Washed 3× with 15% TCA/0.1M Na pyrophosphate (125 μL per wash).
12. Allowed to dry under vacuum for 2–3 minutes.
13. Dried in hood for ~20 minutes.
14. Assembled Wallac Millipore adapter and added 50 μL of scintillant to each well and counted.

IV. FLT-3 Kinase Assay

Flt-3 was expressed as a GST fusion to the Flt-3 kinase domain, and was expressed in baculovirus/insect cells. The following protocol was employed to assay compounds for Flt-3 kinase inhibitory activity:

1. Dilute inhibitors (account for the final dilution into the assay, 1:20)
2. Prepare the appropriate amount of reaction mix at room temperature.
    10× Buffer (20 mM Tris pH.7.4/0.1 M NaCl/1 mM DTT final)
    0.1$MnCl_2$ (5 m M final)
    pEY substrate (75 μg/mL)
    ATP/[$^{33}$P]ATP (0.5 μ/L μCi final)
    BSA (500 μg/mL final)
3. Add 5 μL of the diluted inhibitor to the reaction mix. (Final volume of 5 μL in 50% DMSO). Positive control wells—add blank DMSO (50%).
4. Add 35 μL of the reaction mix to each well of a 96 well plate.
5. Dilute enzyme into enzyme dilution buffer (keep at 4° C.).
6. Add 10 μL of the diluted enzyme to each well and mix (5–10 nM final). Negative control wells—add 10 μL 0.5 M EDTA per well instead (final 100 mM)
7. Incubate at room temperature for 60 min.

8. Stop by the addition of an equal volume (50 μL) of 30% TCA/0.1M Na pyrophosphate.
9. Incubate for 15 min to allow precipitation.
10. Transfer to Millipore filter plate.
11. Wash 3× with 15% TCA/0.1M Na pyrophosphate (125 μL per wash).
12. Allow to dry under vacuum for 2–3 min.
13. Dry in hood for ~20 min.
14. Assemble Wallac Millipore adapter and add 50 μL of scintillant to each well and count.

EXAMPLES

Examples provided are intended to assist in a further understanding of the invention. Particular materials employed, species and conditions are intended to be illustrative of the invention and not limiting of the reasonable scope thereof. The compounds of the instant invention can be prepared by the protocols shown below or by modifications of the procedures reported in WO 01/29025, published 26 Apr. 2001, hereby incoporated by reference.

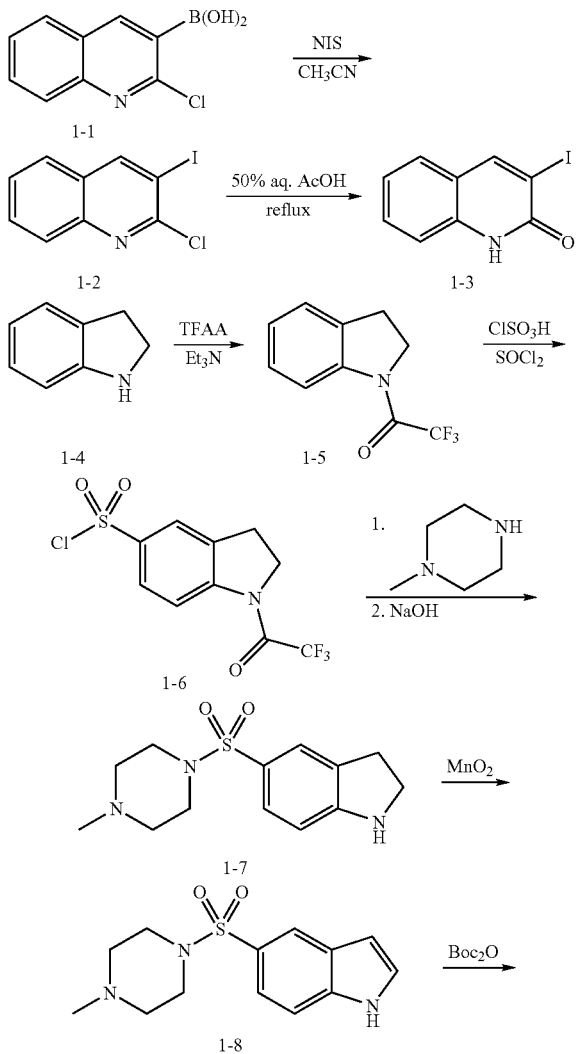

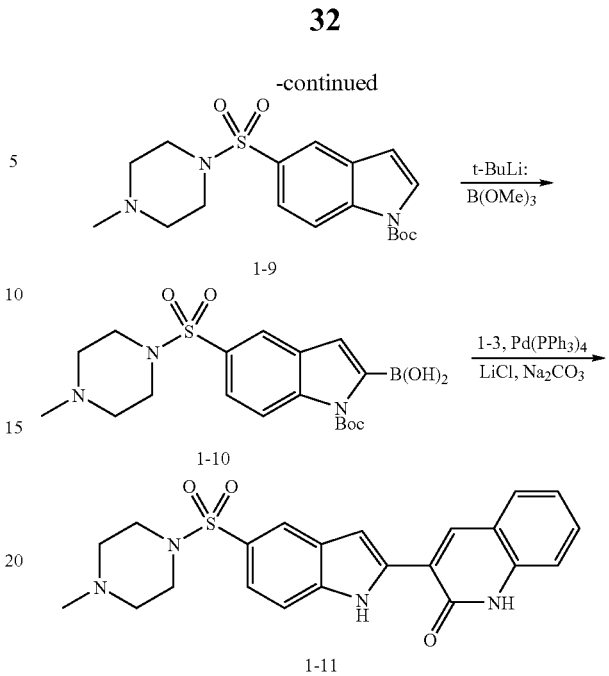

2-chloro-3-iodo-quinoline (1-2)

A suspension of 3-(2-chloro)-quinolineboronic acid (1-1, 5.05 g, 24.3 mmol, 1 equiv, prepared by the method of Marsais, F; Godard, A.; Queguiner, G. J. *Heterocyclic Chem.* 1989, 26, 1589–1594) and N-iodosuccinimide (5.48 g, 24.4 mmol, 1.00 equivalent) in acetonitrile (300 mL) was stirred at 23° C. in the dark for 20 hours. The reaction mixture was concentrated to dryness, and the resulting yellow solid was partitioned between saturated aqueous sodium bicarbonate solution and dichloromethane. The organic layer was washed with water, then dried over magnesium sulfate and concentrated to give 2-chloro-3-iodo-quinoline as a pale yellow solid. $^1$H NMR (400 MHz, CDCl$_3$) δ 8.67 (s, 1H), 7.99 (br d, 1H, J=8.4 Hz), 7.75 (br t, 1H, J=7.7 Hz), 7.72 (br d, 1H, J=7.8 Hz), 7.57 (br t, 1H, J=7.6 Hz).

3-Iodo-1H-quinolin-2-one (1-3)

The 2-chloro-3-iodoquinoline (1-2, 30.0 g) was weighed into a 250 mL flask and suspended in of 50% aqueous acetic acid (125 mL). The mixture was heated to 100° C. and allowed to reflux for 16 hours to completion by TLC analysis of the crude reaction mixture. The mixture was allowed to cool to ambient temperature followed by dilution with 200 mL of water. A suspension of the desired product was isolated by vacuum filtration followed by washing with water (50 mL). The water and traces of acetic acid were removed under vacuum for 5 hours to afford 3-iodo-1H-quinolin-2-one (1-3) as a tan powder. $^1$H NMR (500 MHz, CDCl$_3$) δ 12.13 (br s, 1H), 8.71 (s, 1H), 7.65 (d, 1H, J=7.5 Hz), 7.54 (m, 1H), 7.31 (d, 1H, J=8.0 Hz), 7.20 (m, 1H).

1-(trifluoroacetyl)indoline (1-5)

Trifluoroacetic anhydride (53.3 mL, 378 mmol, 1.50 equiv) was added dropwise over 20 minutes to a solution of indoline (1-4, 30.0 g, 252 mmol, 1 equivalent) and triethylamine (70.2 mL, 503 mmol, 2.00 equiv) in dichlormethane (500 mL) precooled to 0° C. The resulting reaction mixture was warmed to 23° C. and stirred for 30 minutes. The mixture was then washed with aqueous saturated sodium bicarbonate solution (500 mL), dried over sodium sulfate, and concentrated. The resulting solid was suspended in hexane (300 mL), filtered, and dried in vacuo to afford 1-(trifluoroacetyl)indoline (1-5). $^1$H NMR (500 M, CDCl$_3$) δ 8.22 (d, 1H, J=8.5 Hz), 7.27 (m, 2H), 7.16 (t, 1H, J=7.4 Hz), 4.28 (t, 2H, J=8.3 Hz), 3.27 (t,2H), J=7.3 Hz).

1-(trifluoroacetyl)indoline-5-sulfonyl chloride (1-6)

Chlorosulfonic acid (13.3 mL, 200 mmol, 2.00 equiv) was added to a solution of 1-(trifluoroacetyl)indoline (1-5, 21.5 g, 99.9 mmol, 1 equiv)) in thionyl chloride (65.6 mL, 899 mmol, 9.00 equiv) precooled to 0° C. The resulting mixture was stirred for 50 minutes, then poured onto ice (approx. 3 kg). The precipitate was filtered and then dried in vacuo to afford 1-(trifluoroacetyl)indoline-5-sulfonyl chloride (1-6) as an orange solid. $^1$H NMR (500 MHz, CDCl$_3$) δ 8.42 (d, 1H, J=8.5 Hz), 8.00 (d, 1H, J=6.7 Hz), 7.92 (s, 1H), 4.43 (t, 2H, J=8.2 Hz), 3.41 (t, 2H, J=8.2 Hz).

5-[(4-methylpiperazin-1-yl)sulfonyl]indoline (1-7)

N-Methylpiperazine (4.41 mL, 39.7 mmol, 2.00 equiv) was added to a solution of 1-(trifluoroacetyl)indoline-5-sulfonyl chloride (1-6, 6.23 g, 19.9 mmol, 1 equiv) in dichloromethane (50 mL) at 23° C., and the resulting mixture was stirred for 45 minutes. The brown-colored reaction mixture was concentrated and the residue dried in vacuo to give a tan solid. A suspension of the solid in a mixture of 1,4-dioxane (130 mL) and methanol (35 mL) was then treated with aqueous 1N NaOH solution (81.6 mL, 81.6 mmol, 3.00 equiv) and stirred for 1 hour. The mixture was concentrated, and the resulting solids were suspended in diethyl ether (175 mL), filtered, and dried in vacuo. The resulting solid was then partitioned between saturated sodium chloride solution (200 mL) and ethyl acetate (4×100 mL). The organic layer was dried over sodium sulfate and concentrated to provide the 5-[(4-methylpiperazin-1-yl)sulfonyl]indoline (1-7) as a tan solid. $^1$H NMR (500 MHz, DMSO-d$_6$) δ 7.26 (s, 1H), 7.25 (d, 1H, J=7.8 Hz), 6.52 (d, 1H, 8.1 Hz), 6.48 (s, 1H), 3.55 (t, 2H, J=8.8 Hz), 3.00 (t, 2H, J=8.54 Hz), 2.79 (br s,4H), 2.34 (br s, 4H), 2.13 (s, 3H).

5-[(4-methylpiperazin-1-yl)sulfonyl]-1H-indole (1-8)

A suspension of 5-[(4-methylpiperazin-1-yl)sulfonyl]indoline (1-7, 8.00 g, 28.4 mmol, 1 equiv) and MnO$_2$ (8.00 g, 92.0 mmol, 3.24 equiv) in dichloromethane (300 mL) was heated at reflux for 1 hour. More MnO$_2$ (8.00 g, 92.0 mmol, 3:24 equiv) was added, and the resulting suspension was heated for 2 hours. The manganese oxides were filtered off onto a pad of celite and washed with dichloromethane (500 mL). The filtrate was concentrated to give 5-[(4-methylpiperazin-1-yl) sulfonyl]-1H-indole (1-8) as a white solid. 1H NMR (300 MHz, CDCl$_3$) δ 8.59 (br s, 1H), 8.10 (d, 1H, J=1.8 Hz), 7.55 (dd, 1H, J=8.5, 1.8 Hz), 7.46 (d, 1H, J=8.5 Hz), 7.34 (m, 1H), 6.67 (m, 1H), 3.04 (br m, 4H), 2.48 (br t, 4H, J=4.9 Hz), 2.25 (s, 3).

tert-butyl 5-[(4-methylpiperazin-1-yl)sulfonyl]-1H-indole-1-carboxylate (1-9)

4-(Dimethylamino)pyridine (170 mg, 1.40 mmol, 0.05 equiv) was added to a solution of 5-[(4-methylpiperazin-1-yl)sulfonyl]-1H-indole (1-8, 7.80 g, 27.9 mmol, 1 equiv) and di-tert-butyl dicarbonate (6.70 g, 30.7 mmol, 1.1 equiv) in dichloromethane (300 mL) at 23° C. The resulting mixture was stirred for 30 minutes, then partitioned between water (500 mL). The organic layer was dried over sodium sulfate and concentrated to give tert-butyl 5-[(4-methylpiperazin-1-yl)sulfonyl]-1H-indole-1-carboxylate (1-9) as a white solid. $^1$H NMR (300 MHz, CDCl$_3$) δ 8.28 (d, 1H, J=8.9 Hz), 8.00 (d, 1H, J=1.5 Hz), 7.71 (d, 1H, J=4.3 Hz), 7.69 (dd, 1H, J=8.6, 1.8 Hz), 6.66 (dd, 1H, J=3.7, 0.6 Hz), 3.05 (br m, 4H), 2.47 (br t, 4H, J=5.2 Hz), 2.25 (s, 3H), 1.69 (s, 9H).

1-(tert-butoxycarbonyl)-5-[(4-methylpiperazin-1-yl)sulfonyl]-1H-indol-2-ylboronic acid (1-10)

A solution of tert-butyllithium (1.7 M, 6.20 mL, 10.5 mmol, 2.00 equiv) in pentane was added to a solution of tert-butyl 5-[(4-methylpiperazin-1-yl) sulfonyl]-1H-indole-1-carboxylate (1-9, 2.00 g, 5.27 mmol, 1 equiv) in THF (150 mL) at −78° C. The resulting orange-colored reaction mixture was stirred at −78° C. for 1.5 hours before trimethyl borate (1.50 mL, 13.2 mmol, 2.50 equiv) was added. The mixture was warmed to 0° C. where it was stirred for 20 minutes, then partitioned between aqueous half-saturated ammonium chloride solution (200 mL) and EtOAc (2×200 mL). The organic layer was dried over sodium sulfate and concentrated to give 1-(tert-butoxycarbonyl)-5-[(4-methylpiperazin-1-yl)sulfonyl]-1H-indol-2-ylboronic acid (1-10) as a white solid. $^1$H NMR (300 MHz, CDCl$_3$) δ 8.12 (d, 1H, J=8.8 Hz), 8.02 (d, 1H, J=1.6 Hz), 7.71 (d, 7.71 (dd, 1H, J=8.6, 1.8 Hz), 7.49 (s, 1H), 3.05 (br m, 4H), 2.48 (br m, 4H), 2.25 (s, 3H), 1.75 (s, 9H).

3-{5-[(4-methylpiperazin-1-yl)sulfonyl]-1H-indol-2-yl}quinolin-2(1H)-one (1-11)

A solution of 3-iodo-1H-quinolin-2-one (1-3, 1.50 g, 5.53 mmol, 1 equiv), 1-(tert-butoxycarbonyl)-5-[(4-methylpiperazin-1-yl)sulfonyl]-1H-indol-2-ylboronic acid (1-10, 2.00 g, 4.72 mmol, 0.854 equiv), lithium chloride (0.704 g, 16.6 mmol, 3.00 equiv), tetrakis(triphenylphosphine)palladium (0.320 g, 0.277 mmol, 0.050 equiv), and aqueous sodium carbonate solution (2 M, 13.8 mL, 27.6 mmol, 5.00 equiv) in dioxane (50 mL) was heated at 90° C. for 1 hour. 1-(tert-Butoxycarbonyl)-5-[(4-methylpiperazin-1-yl)sulfonyl]-1H-indol-2-ylboronic acid (1-10, 2.00 g total, 4.72 mmol, 0.854 equiv) was then added in two equal portions to the reaction mixture with a 30 minute interval in between additions. Following the last addition, the mixture was heated for 30 minutes. The mixture was then partitioned between brine (150 mL) and EtOAc (2×150 mL). The combined organic layers were dried over sodium sulfate and concentrated. A solution of the residue in dichloromethane (100 mL) was treated with trifluoroacetic acid (100 mL), and the resulting mixture was stirred for 45 minutes, then concentrated. The residue was purified by reverse-phase liquid chromatography (H$_2$O/CH$_3$CN gradient w/0.1% TFA present) to give 3-{5-[(4-methylpiperazin-1-yl)sulfonyl]-1H-indol-2-yl}quinolin-2(1H)one (1-11) as a yellow solid. $^1$H NMR (500 MHz, DMSO-d$_6$) δ 12.26 (s, 1H), 12.15 (s, 1H), 8.62 (s, 1H), 8.04 (br s, 1H), 7.77 (m, 2H), 7.56 (t, 1H, J=7.6 Hz), 7.52 (s, 1H), 7.46 (d, 1H) J=8.5 Hz), 7.40 (d, 1H, J=8.1 Hz), 7.28 (t, 1H, J=7.6 Hz), 3.20–2.00 (br m, 11H).

SCHEME 2

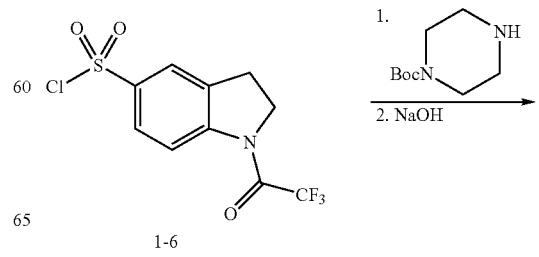

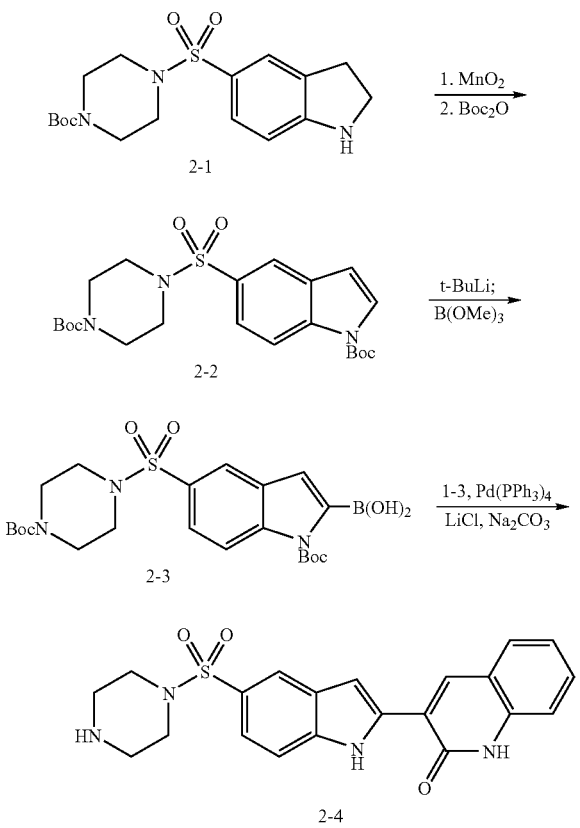

tert-butyl 4-(2,3-dihydro-1H-indol-5-ylsulfonyl)piperazine-1-carboxylate (2-1)

tert-butyl-1-piperazinecarboxylate (5.94 g, 31.9 mmol, 2.00 equiv) was added to a solution of 1-(trifluoroacetyl)indoline-5-sulfonyl chloride (1-6, 5.00 g, 15.9 mmol, 1 equiv) in dichloromethane (50 mL) at 23° C., and the resulting mixture was stirred for 45 minutes. The brown-colored reaction mixture was concentrated and the resulting tan-colored solid dried in vacuo. A solution of the solid in a mixture of 1,4-dioxane (100 mL) and methanol (30 mL) was treated with aqueous 1N NaOH solution (47.9 mL, 47.9 mmol, 3.00 equiv), and the resulting mixture was stirred for 1 hour. The mixture was concentrated, and the resulting solid suspended in diethyl ether (130 mL) and filtered. The filtered solid was then partitioned between aqueous saturated sodium chloride solution (150 mL) and ethyl acetate (4×85 mL). The organic layer was dried over sodium sulfate and concentrated to provide the tert-butyl 4-(2,3-dihydro-1H-indol-5-ylsulfonyl)piperazine-1-carboxylate (2-1) as an off-white solid. $^1$H NMR (300 MHz, CDCl$_3$) δ 7.41 (m, 2H), 6.57 (d, 1H, J=8.9 Hz), 3.69 (t, 2H, J=8.6 Hz), 3.50 (t, 2H, J=4.9 Hz), 3.09 (t, 2H, J=8.6 Hz), 2.93 (t, 2H, J=4.9 Hz) 1.42 (s, 9H).

tert-butyl-5-{[4-(tert-butoxycarbonyl)piperazin-1-yl]sulfonyl}-1H-indole-1-carboxylate (2-2)

A suspension of tert-butyl 4-(2,3-dihydro-1H-indol-5-ylsulfonyl) piperazine-1-carboxylate (2-1, 2.20 g, 5.99 mmol, 1 equiv) and MnO$_2$ (5.00 g, 57.5 mmol, 9.60 equiv) in dichloromethane (200 mL) was heated at reflux for 1 hour. More MnO$_2$ (5.00 g, 57.5 mmol, 9.60 equiv) was added, and the resulting suspension was heated for 2 hour. The manganese oxides were filtered off onto a pad of celite and washed with dichloromethane (500 mL), and the filtrate was concentrated. 4-(Dimethylamino)-pyridine (67 mg, 0.55 mmol, 0.10 equiv) was added to a solution of the residue and di-tert-butyl dicarbonate (1.43 g, 6.57 mmol, 1.10 equiv) in dichloromethane (100 mL) at 23° C. The resulting mixture was stirred for 30 minutes, then concentrated. The residue was purified by flash column chromatography (CH$_2$Cl$_2$ initially, grading to 20% EtOAc in CH$_2$Cl$_2$) to give tert-butyl 5-{[4-(tert-butoxycarbonyl)piperazin-1-yl]sulfonyl}-1H-indole-1-carboxylate (2-2) as a white solid. $^1$H NMR (300 MHz, CDCl$_3$) δ 8.33 (d, 1H, J=8.9 Hz), 8.00 (d, 1H, J=1.5 Hz), 7.73 (d, 1H, J=3.7 Hz), 7.67 (dd, 1H, J=8.8, 1.8 Hz), 6.68 (dd, 1H, J=3.7, 0.6 Hz), 3.50 (br t, 4H, J=5.2 Hz), 2.97 (br t, 4H, J=4.9 Hz), 1.69 (s, 9H), 1.38 (s, 9H).

1-(tert-butoxycarbonyl)-5-{[4-(tert-butoxycarbonyl)piperazin-1-yl]sulfonyl}-1H-indol-2-ylboronic acid (2-3)

A solution of tert-butyllithium (1.7 M, 4.55 mL, 7.73 mmol, 2.00 equiv) in pentane was added to a solution of tert-butyl 5-{[4-(tert-butoxycarbonyl) piperazin-1-yl]sulfonyl}-1H-indole-1-carboxylate (2-2, 1.80 g, 3.87 mmol, 1 equiv) in THF (100 mL) at −78° C. The resulting orange-colored reaction mixture was stirred at −78° C. for 1.5 hour before trimethyl borate (1.10 mL, 9.66 mmol, 2.50 equiv) was added. The mixture was warmed to 0° C. and stirred for 20 minutes. Boron trifluoride diethyl etherate (1.20 mL, 9.66 mmol, 2.50 equiv) was then added, and the resulting mixture was partitioned between aqueous half-saturated ammonium chloride solution (200 mL) and EtOAc (2×200 mL). The organic layer was dried over sodium sulfate and concentrated to give 1-(tert-butoxycarbonyl)-5-{[4-(tert-butoxycarbonyl) piperazin-1-yl]sulfonyl}-1H-indol-2-ylboronic acid (2-3) as a tan solid. LCMS [M+H]$^+$ observed=510.3; calculated=510.4.

3-[5-(piperazin-1-ylsulfonyl)-1H-indol-2-yl]quinolin-2(1H)-one (2-4)

1-(tert-Butoxycarbonyl)-5-{[4-(tert-butoxycarbonyl)piperazin-1-yl]sulfonyl}-1H-indol-2-ylboronic acid (2-3, 1.88 g, 3.69 mmol, 2.0 equiv) was added in four equal portions at 30 minute intervals to a solution of 3-iodo-1H-quinolin-2-one (1-3, 0.500 g, 1.84 mmol, 1 equiv), lithium chloride (0.235 g, 5.54 mmol, 3.00 equiv), tetrakis(triphenylphosphine)palladium (0.107 g, 0.093 mmol, 0.050 equiv), and aqueous sodium carbonate solution (2 M, 4.61 mL, 9.22 mmol, 5.00 equiv) in dioxane (50 mL) at 90° C. The reaction mixture was heated for 2 h at 90° C. following the final addition. The mixture was then partitioned between brine (100 mL) and EtOAc (2×100 mL). The combined organic layers were dried over sodium sulfate and concentrated. A solution of the residue in dichloromethane (100 mL) was treated with trifluoroacetic acid (100 mL), and the resulting mixture was stirred for 45 minutes, then concentrated. The residue was purified by reverse-phase liquid chromotography (H$_2$O/CH$_3$CN gradient w/0.1% TFA present) to give 3-[5-(piperazin-1-ylsulfonyl)-1H-indol-2-yl]quinolin-2(1H)-one (2-4) as a yellow solid. $^1$H NMR (500 MHz, DMSO-d$_6$) δ 12.23 (br s, 1H), 12.11 (s, 1H), 8.62 (s, 1H), 8.00 (br s, 1H), 7.77 (d, 1H, J=7.8 Hz), 7.74 (d, 1H, J=8.6 Hz), 7.56 (t, 1H, J=7.8 Hz), 7.51 (s, 1H), 7.44 (d, 1H, J=8.6 Hz), 7.40 (d, 1H, J=8.1 Hz), 7.27 (t, 1H, J=7.8 Hz), 2.77 (m, 4H), 2.71 (m, 4H).

The following compounds were prepared by simple modifications of the above procedures.

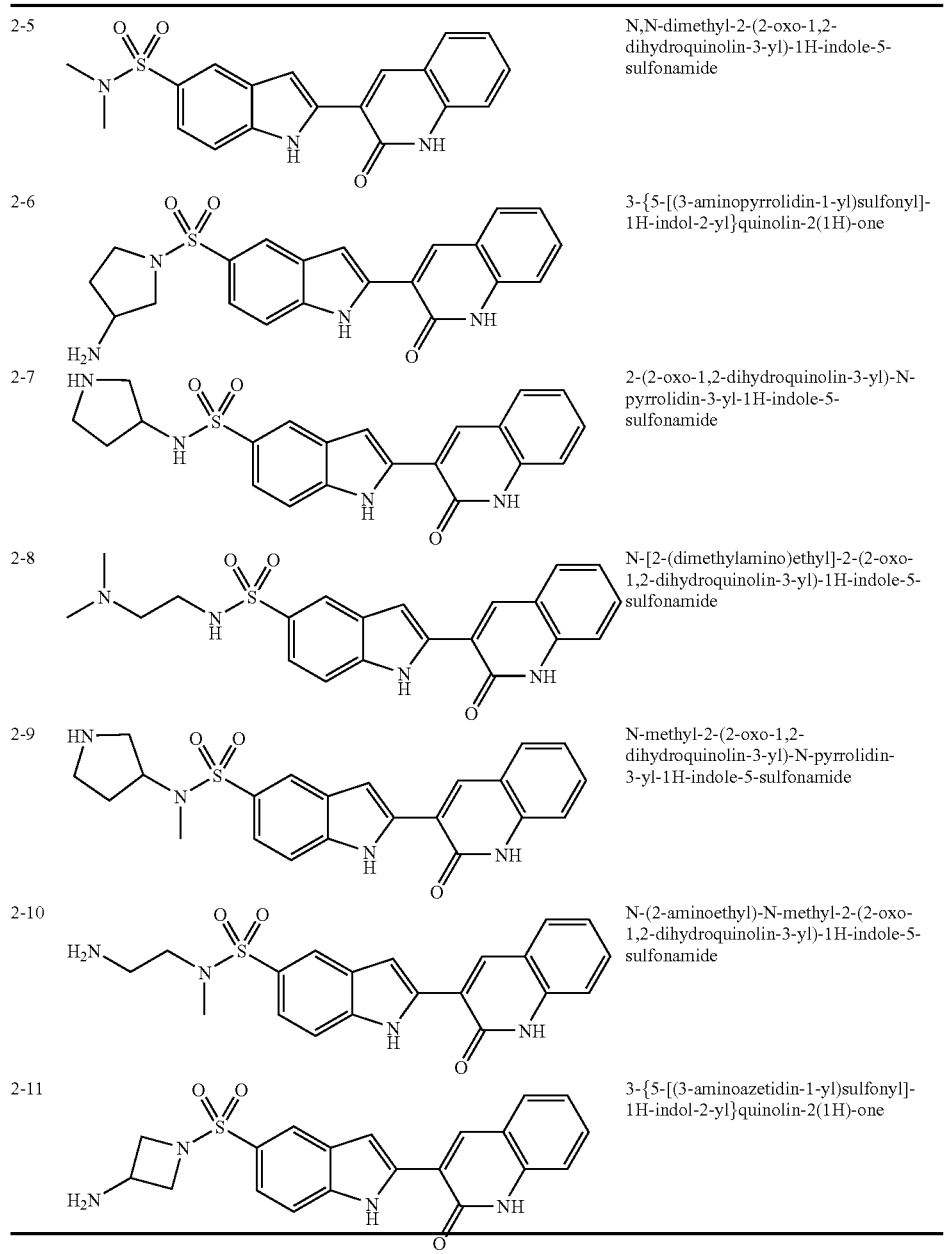
In addition, the following compounds can be readily prepared by simple modifications of the examples and schemes illustrated above, and are within the scope of the present invention.
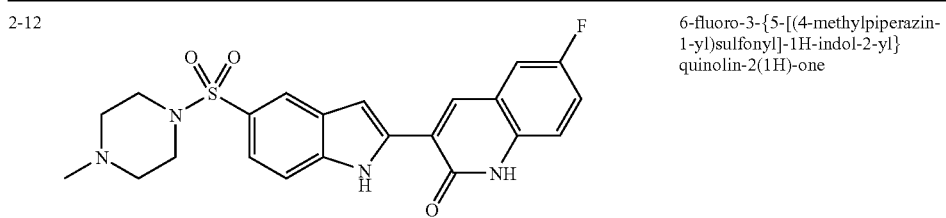

| # | Name |
|---|---|
| 2-13 | 7-fluoro-3-[5-(piperazin-1-ylsulfonyl)-1H-indol-2-yl]quinolin-2(1H)-one |
| 2-14 | 2-(5-fluoro-2-oxo-1,2-dihydroquinolin-3-yl)-N-methyl-N-pyrrolidin-3-yl-1H-indole-5-sulfonamide |
| 2-15 | 3-{5-[(3-aminopyrrolidin-1-yl)sulfonyl]-1H-indol-2-yl}-5-fluoroquinolin-2(1H)-one |
| 2-16 | 2-(7-chloro-2-oxo-1,2-dihydroquinolin-3-yl)-N-[2-(dimethylamino)ethyl]-1H-indole-5-sulfonamide |
| 2-17 | 6-chloro-3-{5-[(4-methylpiperazin-1-yl)sulfonyl]-1H-indol-2-yl}quinolin-2(1H)-one |
| 2-18 | 3-{6-fluoro-5-[(4-methylpiperazin-1-yl)sulfonyl]-1H-indol-2-yl}quinolin-2(1H)-one |
| 2-19 | 3-[6-chloro-5-(piperazin-1-ylsulfonyl)-1H-indol-2-yl]quinolin-2(1H)-one |
| 2-20 | 4-fluoro-N-methyl-2-(2-oxo-1,2-dihydroquinolin-3-yl)-N-pyrrolidin-3-yl-1H-indole-5-sulfonamide |

| | | |
|---|---|---|
| 2-21 | 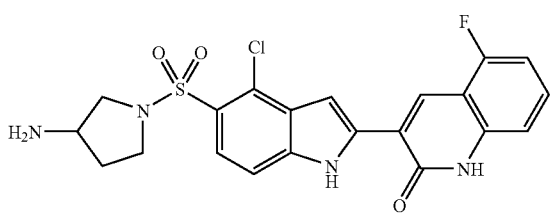 | 3-{5-[(3-aminopyrrolidin-1-yl)sulfonyl]-4-chloro-1H-indol-2-yl}-5-fluoroquinolin-2(1H)-one |
| 2-22 | 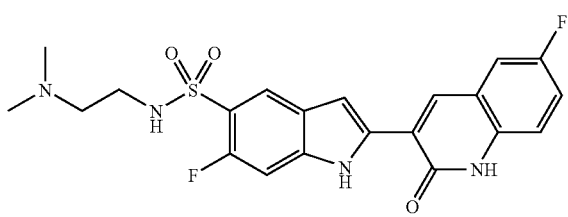 | N-[2-(dimethylamino)ethyl]-6-fluoro-2-(6-fluoro-2-oxo-1,2-dihydroquinolin-3-yl)-1H-indole-5-sulfonamide |
| 2-23 | 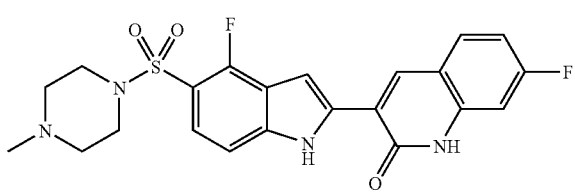 | 7-fluoro-3-{4-fluoro-5-[4-methylpiperazin-1-yl)sulfonyl]-1H-indol-2-yl}quinolin-2(1H)-one |
| 2-24 | 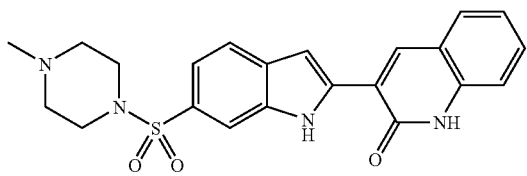 | 3-[6-(piperazin-1-ylsulfonyl)-1H-indol-2-yl]quinolin-2(1H)-one |
| 2-25 | 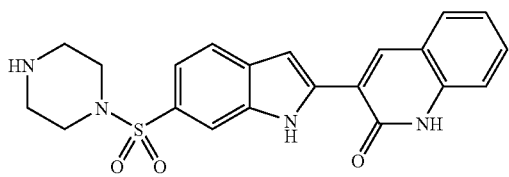 | 3-[6-(piperazin-1-ylsulfonyl)-1H-indol-2-yl]quinolin-2(1H)-one |
| 2-26 |  | N-methyl-2-(2-oxo-1,2-dihydroquinolin-3-yl)-N-pyrrolidin-3-yl-1H-indole-6-sulfonamide |
| 2-27 | 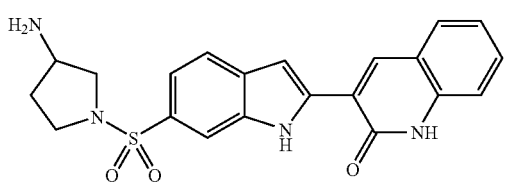 | 3-{6-[(3-aminopyrrolidin-1-yl)sulfonyl]1H-indol-2-yl}quinolin-2(1H)-one |
| 2-28 | 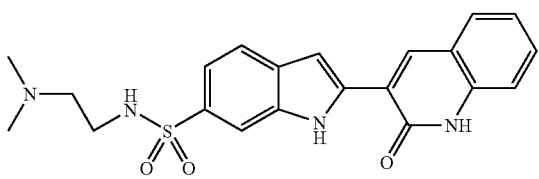 | N-[2-(dimethylamino)ethyl]-2-(2-oxo-1,2-dihydroquinolin-3-yl)-1H-indole-6-sulfonamide |

-continued

| | | |
|---|---|---|
| 2-29 | | 3-[4-(piperazin-1-ylsulfonyl)-1H-indol-2-yl]quinolin-2(1H)-one |
| 2-30 | | 3-[4-(piperazin-1-ylsulfonyl)-1H-indol-2-yl]quinolin-2(1H)-one |
| 2-31 | | N-methyl-2-(2-oxo-1,2-dihydroquinolin-3-yl)-N-pyrrolidin-3-yl-1H-indole-4-sulfonamide |
| 2-32 | | 3-{4-[(3-aminopyrrolidin-1-yl)sulfonyl]-1H-indol-2-yl}quinolin-2(1H)-one |
| 2-33 | | N-[2-(dimethylamino)ethyl]-2-(2-oxo-1,2-dihydroquinolin-3-yl)-1H-indole-4-sulfonamide |
| 2-34 | | 3-{3-fluoro-5-[(4-methylpiperazin-1-yl)sulfonyl]-1H-indol-2-yl}quinolin-2(1H)-one |

| | | |
|---|---|---|
| 2-35 | 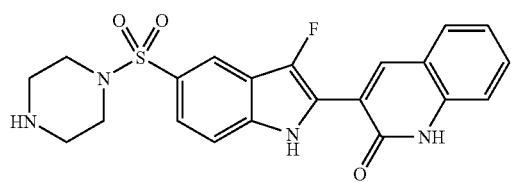 | 3-[3-fluoro-5-(piperazin-1-ylsulfonyl)-1H-indol-2-yl]quinolin-2(1H)-one |
| 2-36 | 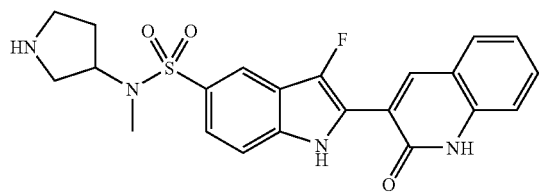 | 3-fluoro-N-methyl-2-(2-oxo-1,2-dihydroquinolin-3-yl)-N-pyrrolidin-3-yl-1H-indole-5-sulfonamide |
| 2-37 | 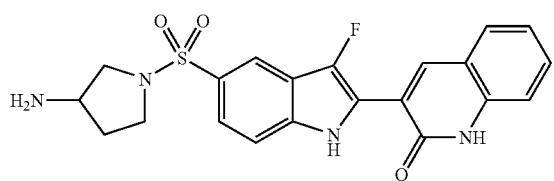 | 3-{5-[(3-aminopyrrolidin-1-yl)sulfonyl]-3-fluoro-1H-indol-2-yl}quinolin-2(1H)-one |
| 2-38 | 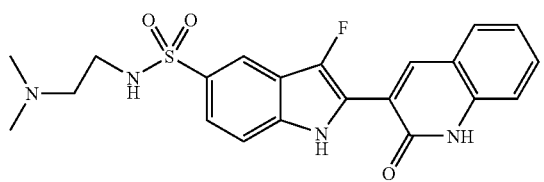 | N-[2-(dimethylamino)ethyl]-3-fluoro-2-(2-oxo-1,2-dihydroquinolin-3-yl)-1H-indole-5-sulfonamide |
| 2-39 | 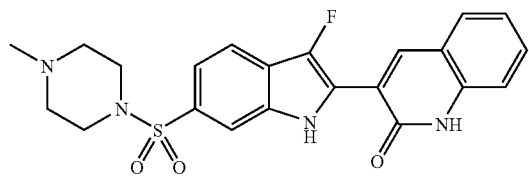 | 3-{3-fluoro-6-[(4-methylpiperazin-1-yl)sulfonyl]-1H-indol-2-yl}quinolin-2(1H)-one |
| 2-40 | 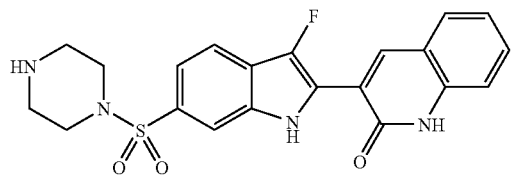 | 3-[3-fluoro-6-(piperazin-1-ylsulfonyl)-1H-indol-2-yl]quinolin-2(1H)-one |
| 2-41 | 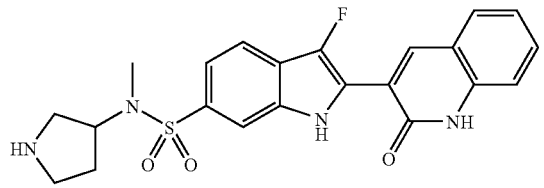 | 3-fluoro-N-methyl-2-(2-oxo-1,2-dihydroquinolin-3-yl)-N-pyrrolidin-3-yl-1H-indole-6-sulfonamide |
| 2-42 | 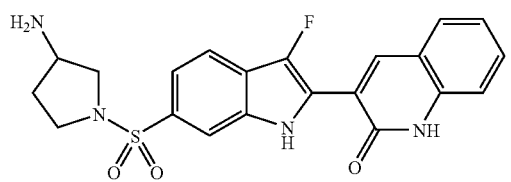 | 3-{6[(3-aminopyrrolidin-1-yl)sulfonyl]-3-fluoro-1H-indol-2-yl}quinolin-2(1H)-one |

| | |
|---|---|
| 2-43 |  N-[2-(dimethylamino)ethyl]-3-fluoro-2-(2-oxo-1,2-dihydroquinolin-3-yl)-1H-indole-6-sulfonaimde |

The invention claimed is:

1. A compound of Formula I

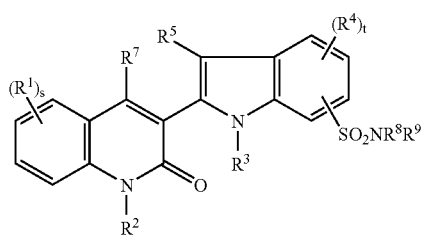

or a pharmaceutically acceptable salt or stereoisomer thereof, wherein
a is 0 or 1;
b is 0 or 1;
m is 0, 1, or 2;
s is 0 or 1;
t is 0 or 1
$R^1$ and R4 are independently:
  6) halo,
$R^2$ and $R^3$ are independently:
  1) H,
  2) $(C=O)O_aC_1-C_6$ alkyl, optionally substituted with aryl,
  3) $(C=O)O_a$aryl,
  4) $C_1-C_6$ alkyl, optionally substituted with aryl, or
  5) $SO_2R^a$;
$R^5$ and $R^7$ are independently H, halo, or $C_1-C_6$ alkyl;
$R^8$ and $R^9$ are independently:
  1) H,
  5) $C_1-C_{10}$ alkyl,
  6) aryl,
  9) heterocyclyl,
  12) $C_1-C_{10}$ alkyl-$NR^b_2$, or
$R^8$ and $R^9$ are taken together with the nitrogen to which they are attached to form a monocyclic heterocycle with 5–7 members in each ring and optionally containing, in addition to the nitrogen, one or two additional heteroatoms selected from N, O and S, wherein said monocyclic heterocycle is optionally substituted with one or more substituents selected from $R^c$;
$R^a$ is $C_1-C_6$ alkyl, aryl, or benzyl;
$R^b$ is H, $C_1-C_6$ alkyl, aryl, or benzyl;
$R^c$ is:
  1) $(C=O)_aO_b(C_1-C_1O)$alkyl, optionally substituted with $NR^b_2$,
  2) oxo,
  3) OH,
  4) halo,
  5) CN,
  6) $SO_mR^a$,
  7) aryl,
  8) $NR^b_2$,
  9) $C(O)R^a$,
  10) $(C_0-C_6)$alkyl-$CO_2R^a$,
  11) C(O)H, or
  12) $(C_0-C_6)$alkyl-$CO_2$.

2. The compound according to claim 1 or a pharmaceutically acceptable salt or stereoisomer thereof, wherein
s is 0 or 1;
t is 0 or 1;
$R^1$ and $R^4$ are independently:
  6) halo,
$R^2$ and $R^3$ are independently:
  1) H,
  2) $(C=O)O_aC_1-C_3$ alkyl, optionally substituted with aryl,
  3) $(C=O)O_a$ aryl,
  4) $C_1-C_3$ alkyl, optionally substituted with aryl, or
  5) $SO_2R^a$;
$R^5$ and $R^7$ are independently H, halo, or $C_1-C_6$ alkyl;
$R^8$ and $R^9$ are independently:
  1) H,
  5) $C_1-C_6$alkyl,
  6) aryl,
  9) heterocyclyl,
  12) $C_1-C_6$ alkyl-$NR^b_2$, or
$R^8$ and $R^9$ are taken together with the nitrogen to which they are attached to form a 5–7 membered heterocycle optionally containing, in addition to the nitrogen, one or two additional heteroatoms selected from N, O and S, and optionally substituted with one to three substituents selected from $R^c$;
$R^a$ is $C_1-C_6$ alkyl, aryl, or benzyl;
$R^b$ is H, $C_1-C_6$ alkyl, aryl, or benzyl;
$R^c$ is:
  1) $(C=O)_aO_b(C_1-C_6)$alkyl, optionally substituted with $NR^b_2$,
  2) oxo,
  3) OH,
  4) halo,
  5) CN,
  6) $SO_mR^a$,
  7) aryl,
  8) $NR^b_2$,
  9) $C(O)R^a$,
  10) $(C_0-C_6)$alkyl-$CO_2R^a$,
  11) C(O)H, or
  12) $(C_0-C_6)$alkyl-$CO_2H$.

3. The compound according to claim 2 or a pharmaceutically acceptable salt or stereoisomer thereof, wherein
$R^1$ and $R^4$ are independently:
  5) halo,
$R^2$ and $R^3$ are independently H or $C_1-C_3$ alkyl;
$R^5$ is H, $C_1-C_3$ alkyl, or halogen;
$R^7$ is H;

$R^8$ and $R^9$ are independently:
1) H,
5) $C_1$–$C_6$alkyl,
6) aryl,
9) heterocyclyl,
12) $C_0$–$C_6$ alkyl-$NR^b{}_2$, or $R^8$ and $R^9$ are taken together with the nitrogen to which they are attached to form a 5–7 membered heterocycle optionally containing, in addition to the nitrogen, one or two additional heteroatoms selected from N, O and S, and optionally substituted with one to three substituents selected from $R^c$;

$R^a$ is $C_1$–$C_6$ alkyl, aryl, or benzyl;
$R^b$ is H, $C_1$–$C_6$ alkyl, aryl, or benzyl;
$R^c$ is:
1) $(C=O)_aO_b(C_1$–$C_6)$alkyl, optionally substituted with $NR^b{}_2$,
2) oxo,
3) OH,
4) halo,
5) CN,
6) $SO_mR^a$,
7) aryl,
8) $NR^b{}_2$,
9) $C(O)R^a$,
10) $(C_0$–$C_6)$alkyl-$CO_2R^a$,
11) C(O)H, or
12) $(_0$–$C_6)$ alkyl-$CO_2H$.

4. A compound according to claim 1 selected from:
3-{5-[(4-methylpiperazin-1-yl)sulfonyl]-1H-indol-2-yl}quinolin-2(1H)-one;
3-[5-(piperazin-1-ylsulfonyl)-1H-indol-2-yl]quinolin-2(1H)-one;
3-{5-[(3-aminopyrrolidin-1-yl)sulfonyl]-1H-indol-2-yl}quinolin-2(1H)-one;
N-[2-(dimethylamino)ethyl]-2-(2-oxo-1,2-dihydroquinolin-3-yl)-1H-indole-5-sulfonamide; and
N-methyl-2-(2-oxo-1,2-dihydroquinolin-3-yl)-N-pyrrolidin-3-yl-1H-indole-5-sulfonamide,
or a pharmaceutically acceptable salt or stereoisomer thereof.

5. A pharmaceutical composition which is comprised of a compound in accordance with claim 1 and a pharmaceutically acceptable carrier.

6. A method of treating acute myeloid leukemia which comprises administering a therapeutically effective amount of a compound of claim 1.

* * * * *